United States Patent
Choe et al.

(10) Patent No.: US 11,512,126 B2
(45) Date of Patent: Nov. 29, 2022

(54) AB6 FAMILY DESIGNER LIGANDS OF TGF-β SUPERFAMILY

(71) Applicants: MOGAM INSTITUTE FOR BIOMEDICAL RESEARCH, Yongin-si (KR); JOINT CENTER FOR BIOSCIENCES, Incheon (KR)

(72) Inventors: Sen Yon Choe, Yongin-si (KR); Chi Hoon Ahn, Yongin-si (KR); Ho Cheol Kim, Yongin-si (KR); Hyeon Jin Kim, Yongin-si (KR)

(73) Assignees: MOGAM INSTITUTE FOR BIOMEDICAK RESEARCH, Yongin-si (KR); JOINT CENTER FOR BIOSCIENCES, Incheon (KR)

( * ) Notice: Subject to any disclaimer, the term of this patent is extended or adjusted under 35 U.S.C. 154(b) by 346 days.

(21) Appl. No.: 16/305,771

(22) PCT Filed: May 31, 2017

(86) PCT No.: PCT/KR2017/005703
§ 371 (c)(1),
(2) Date: Nov. 29, 2018

(87) PCT Pub. No.: WO2017/209519
PCT Pub. Date: Dec. 7, 2017

(65) Prior Publication Data
US 2020/0325216 A1 Oct. 15, 2020

Related U.S. Application Data

(60) Provisional application No. 62/343,326, filed on May 31, 2016.

(51) Int. Cl.
*C07K 16/22* (2006.01)
*C07K 16/28* (2006.01)

(52) U.S. Cl.
CPC .......... *C07K 16/22* (2013.01); *C07K 16/2863* (2013.01); *C07K 2317/24* (2013.01)

(58) Field of Classification Search
CPC .......................... C07K 16/22; C07K 16/2863; C07K 2317/24; C07K 2319/00
See application file for complete search history.

(56) References Cited

U.S. PATENT DOCUMENTS

| 5,756,308 A | 5/1998 | Wolfman et al. |
| 8,952,130 B2 * | 2/2015 | Choe ................. A61P 35/00 530/350 |
| 2005/0250936 A1 | 11/2005 | Oppermann et al. |
| 2015/0239950 A1 | 8/2015 | Choe et al. |

FOREIGN PATENT DOCUMENTS

KR  10-2011-0121642 A  11/2011

OTHER PUBLICATIONS

Radhika V. Korupolu et al., "Activin A/Bone Morphogenetic Protein (BMP) Chimeras Exhibit BMP-like Activity and Antagonize Activin and Myostatin," The Journal of Biological Chemistry, Feb. 15, 2008, pp. 3782-3790, vol. 283, No. 7.
G. Jimenez et al., "Activin A/BMP2 chimera AB235 drives efficient redifferentiation of long term cultured autologous chondrocytes," Scientific Reports, Nov. 13, 2015, pp. 1-8, vol. 5, No. 16400.
International Search Report of PCT/KR2017/005703 dated Sep. 12, 2017.
Byung-Hak Yoon et al., "An Activin A/BMP2 chimera displays bone healing properties superior to those of BMP2", Journal of Bone and Mineral Research, vol. 29, No. 9, Sep. 2014, pp. 1950-1959 (20 pages total).
George P. Allendorph et al., "BMP-3 and BMP-6 Structures Illuminate the Nature of Binding Specificity with Receptors", Biochemistry, vol. 46, No. 43, 2007, pp. 12238-12247 (10 pages total).
George P. Allendorph et al., "Designer TGFβ Superfamily Ligands with Diversified Functionality", PLOS ONE, vol. 6, Issue 11, Nov. 4, 2011 (12 pages total).
Witek Kwiatkowski et al., "Engineering TGF-β superfamily ligands for clinical applications", Trends in Pharmacological Sciences., vol. 35, No. 12, Dec. 2014, pp. 648-657 (10 pages total).
Communication dated Nov. 15, 2019, from the European Patent Office in application No. 17807012.4.

* cited by examiner

*Primary Examiner* — Jessica H Roark
*Assistant Examiner* — Cheom-Gil Cheong
(74) *Attorney, Agent, or Firm* — Sughrue Mion, PLLC

(57) ABSTRACT

A non-naturally occurring chimeric polypeptide having an activity provided by a TGF-beta family member is disclosed. The chimeric polypeptide of an embodiment comprises two or more domains or fragments from parental TGF-beta proteins operably linked such that the resulting polypeptide is capable of modulating a pathway associated with a TGF-beta family member. In one embodiment, the pathway is a SMAD or DAXX pathway.

2 Claims, 17 Drawing Sheets

Specification includes a Sequence Listing.

[Fig. 1]
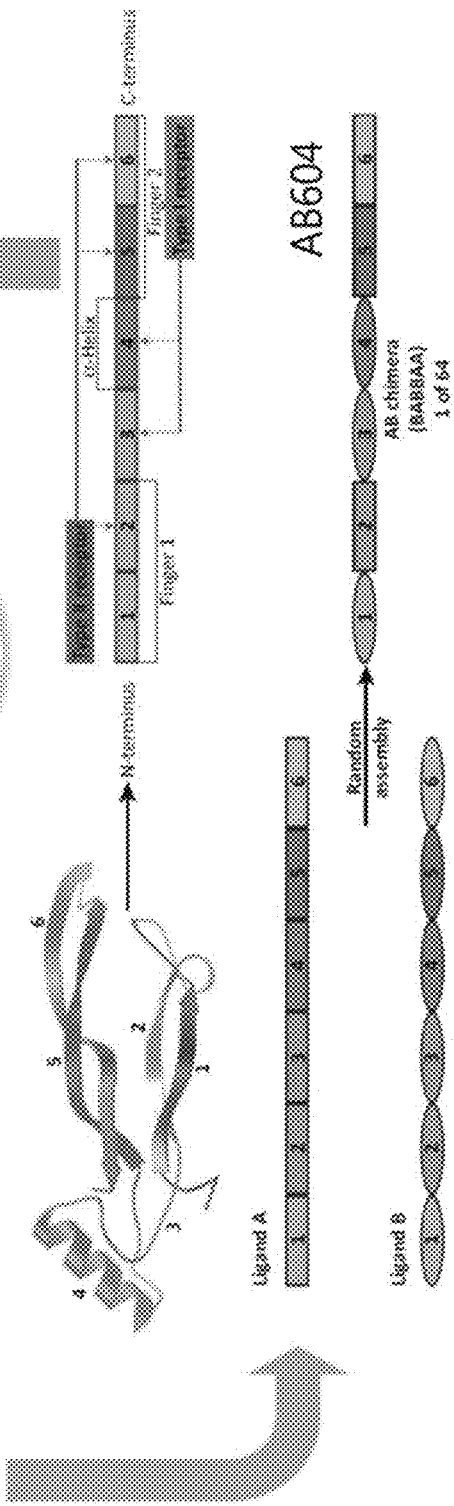

[Fig. 2]

BMP-2: SEQ ID NO: 13, BMP-3: SEQ ID NO: 14, BMP-4: SEQ ID NO: 15, BMP-5: SEQ ID NO: 16, BMP-6: SEQ ID NO: 2, BMP-7: SEQ ID NO: 17, BMP-8: SEQ ID NO: 18, BMP-9: SEQ ID NO: 19, BMP-10: SEQ ID NO: 20, BMP-15: SEQ ID NO: 21, GDF-1: SEQ ID NO: 22, GDF-3: SEQ ID NO: 23, GDF-5: SEQ ID NO: 24, GDF-6: SEQ ID NO: 25, GDF-7: SEQ ID NO: 26, GDF-8: SEQ ID NO: 27, GDF-9: SEQ ID NO: 28, GDF-10: SEQ ID NO: 29, GDF-11: SEQ ID NO: 30, GDF-15: SEQ ID NO: 31, NODAL: SEQ ID NO: 32, ACTIVIN-A: SEQ ID NO: 4, ACTIVIN-B: SEQ ID NO: 6, ACTIVIN-C: SEQ ID NO: 8, ACTIVIN-E: SEQ ID NO: 10, INHIBIN-A: SEQ ID NO: 33, TGF-beta1: SEQ ID NO: 34, TGF-beta2: SEQ ID NO: 35, TGF-beta3: SEQ ID NO: 36

[Fig. 3]
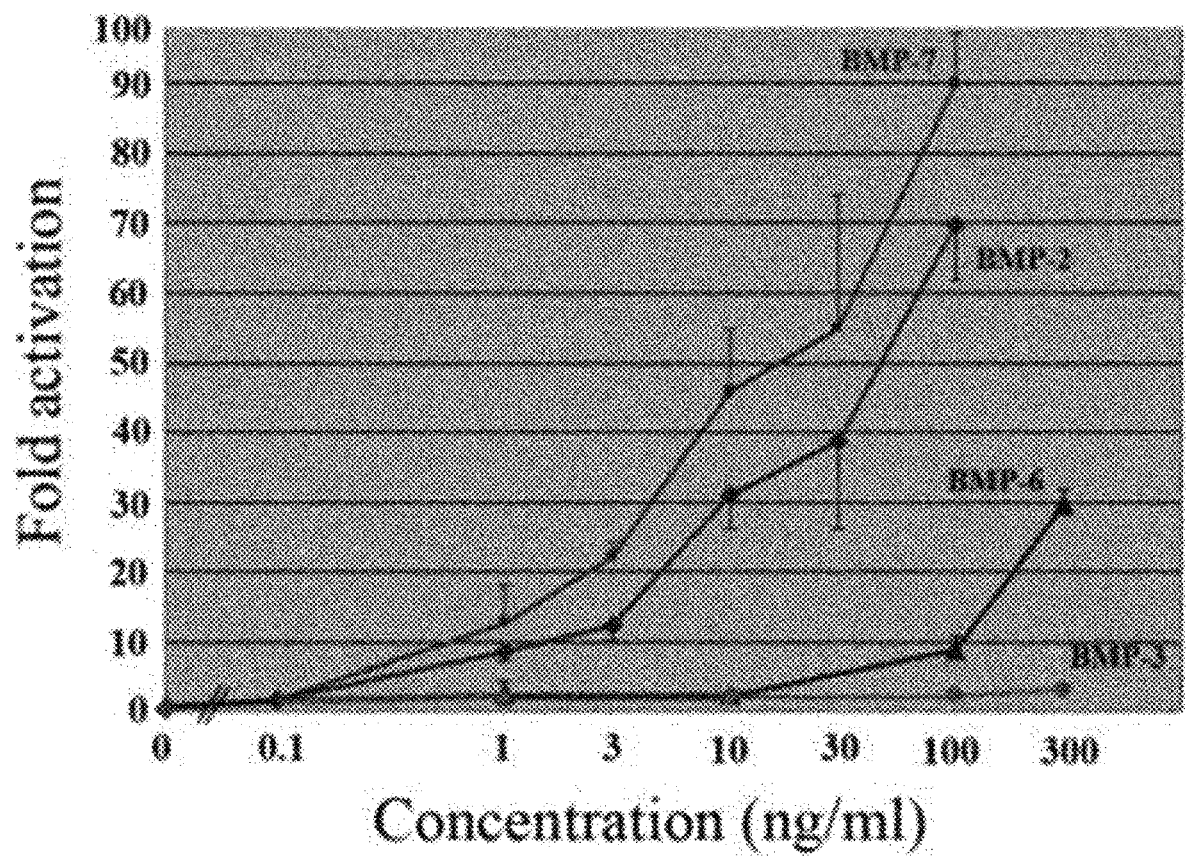

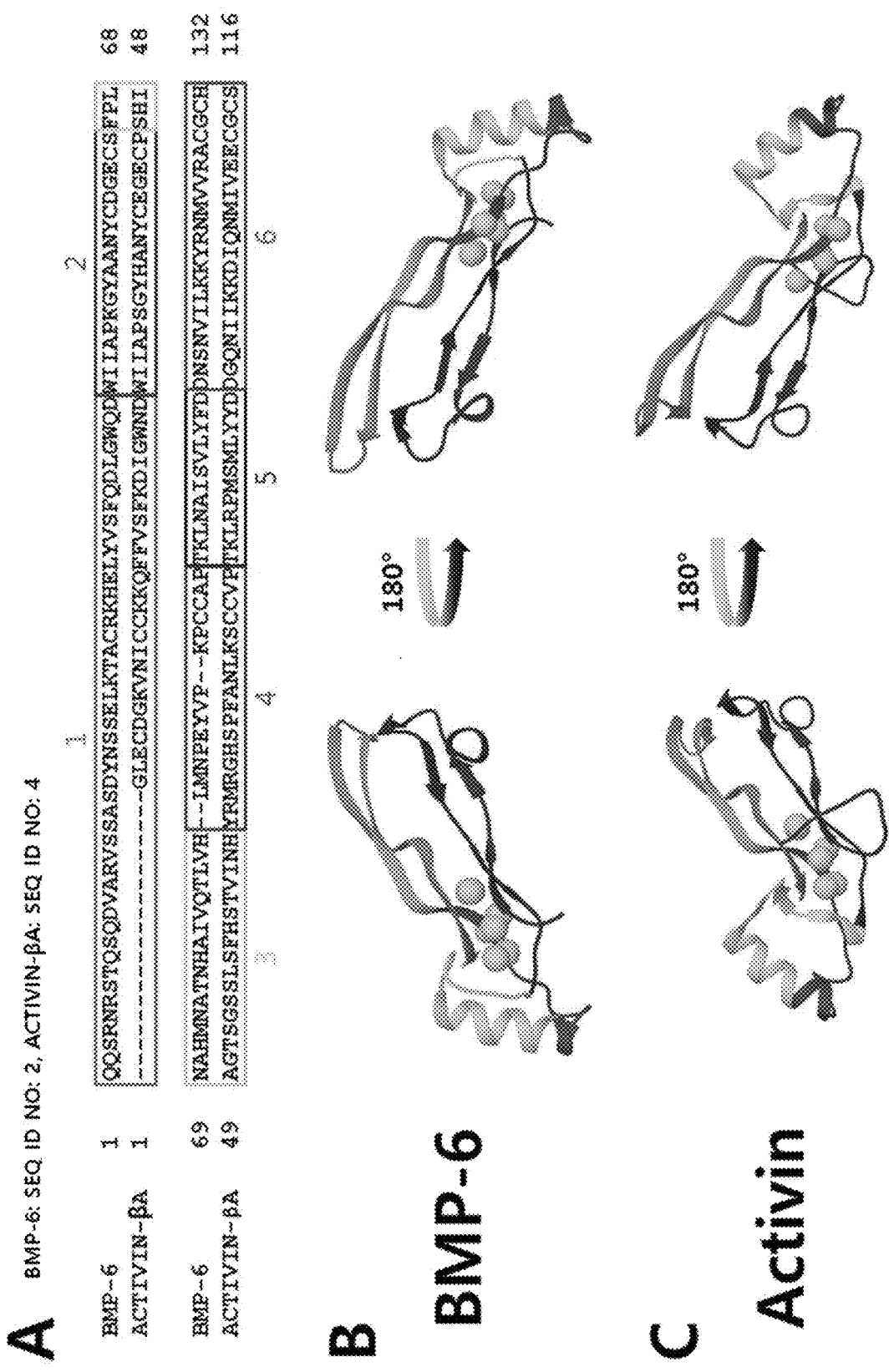

[Fig. 5]

Amino acids sequence of AB604 (SEQ ID NO: 12)

MQQSRNRSTQSQDVARVSSASDYNSSELKTACRKHELYVSFQDLGWQDWIIAPSGYHANYCEGECPFPLNAHM
NATNHAIVQTLVHLMNPEYVPKPCCAPTKLRPMSMLYYDDGQNIIKKDIQNMIVEECGCS

Black: BMP6 Sequence
Gray: Activin A Sequence

[Fig. 6]
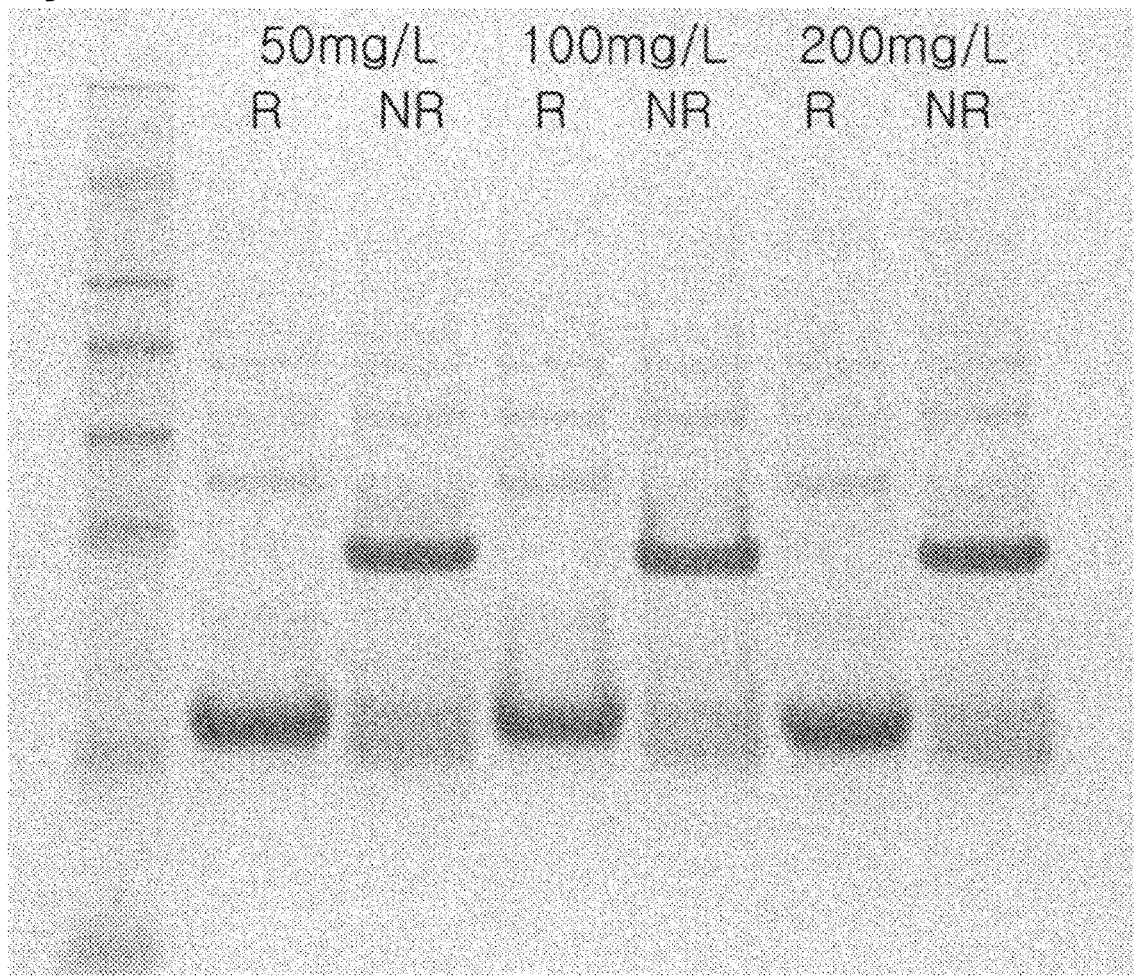

[Fig. 7]
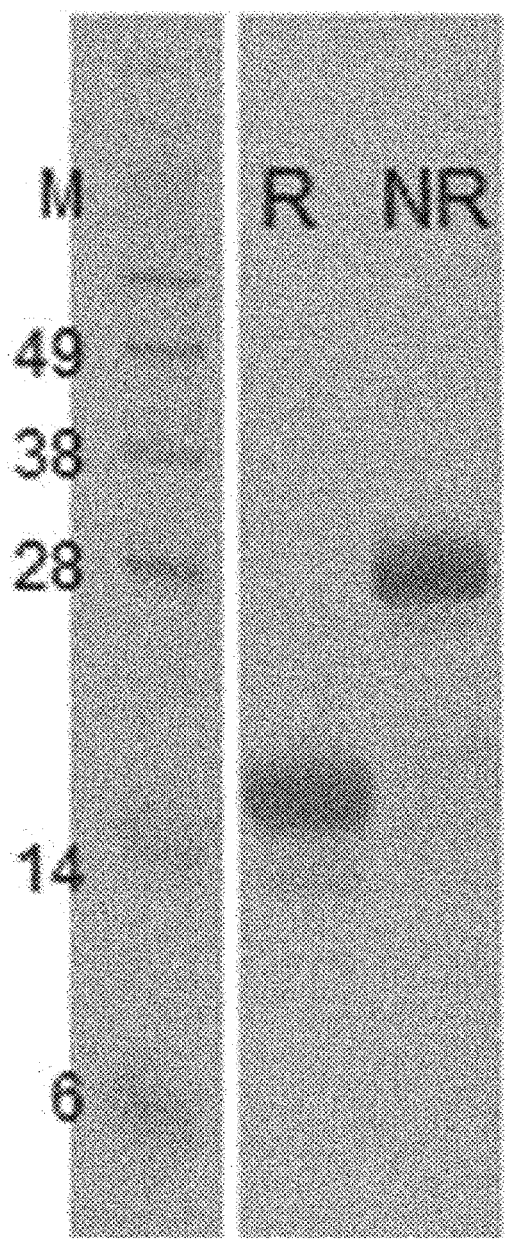

[Fig. 8]
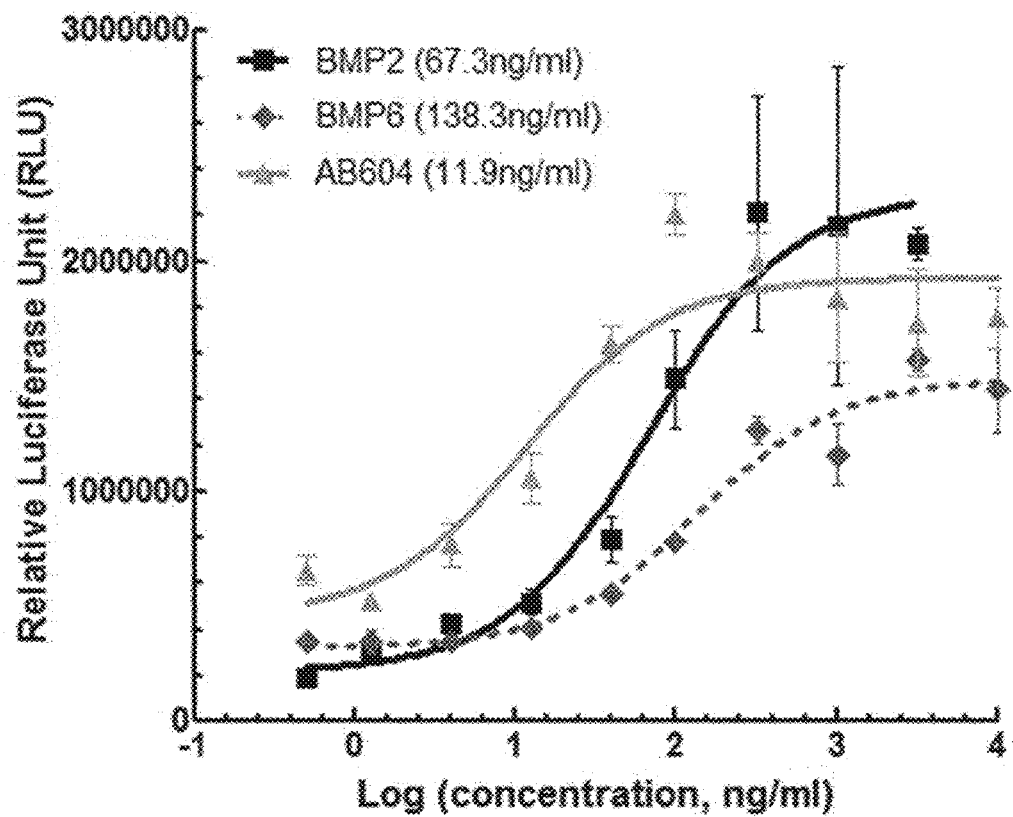

[Fig. 9]
Signaling of AB204 and AB604 via SMAD1
C2C12/Id1-luc,SMAD1
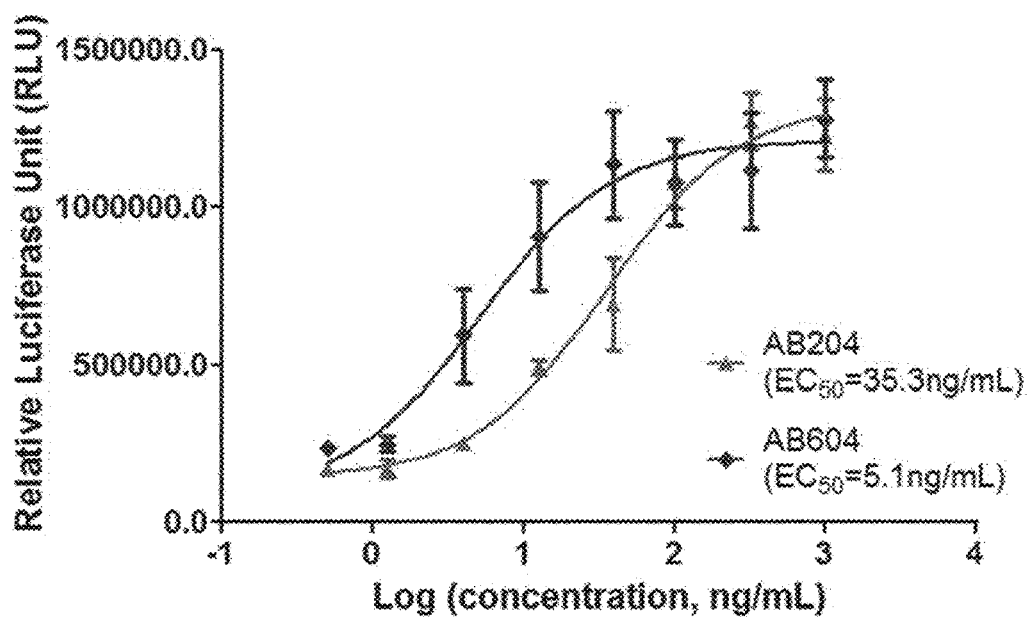
[Fig. 10]
Signaling of AB604 via SMAD2
HEK293T/A3-Lux,Fast2
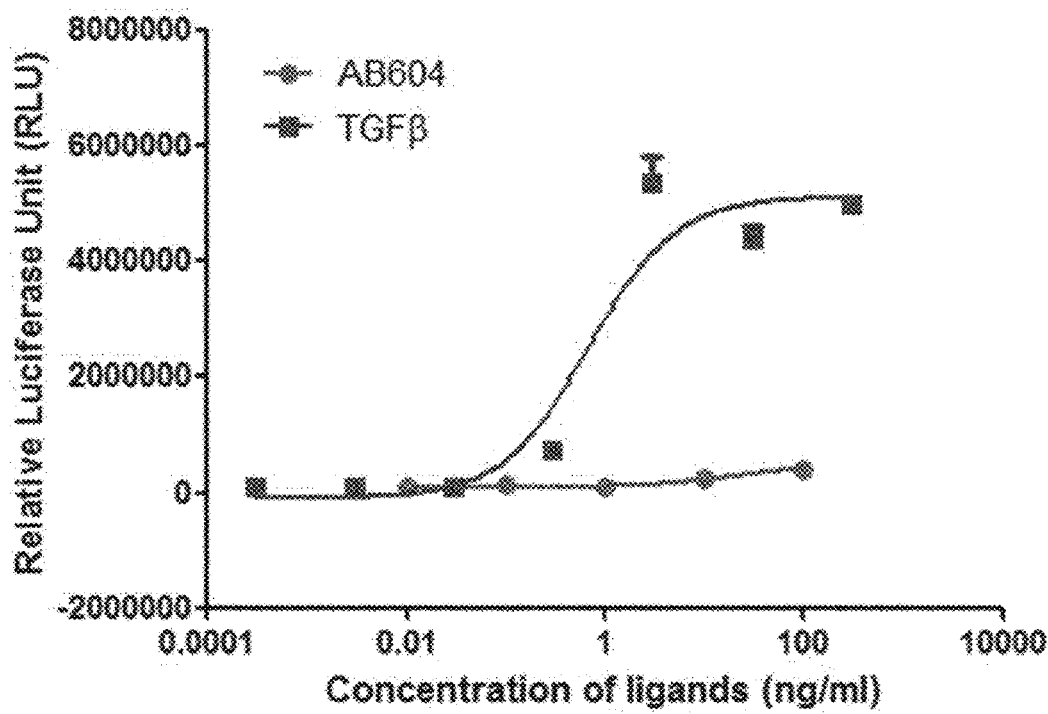

[Fig. 11]
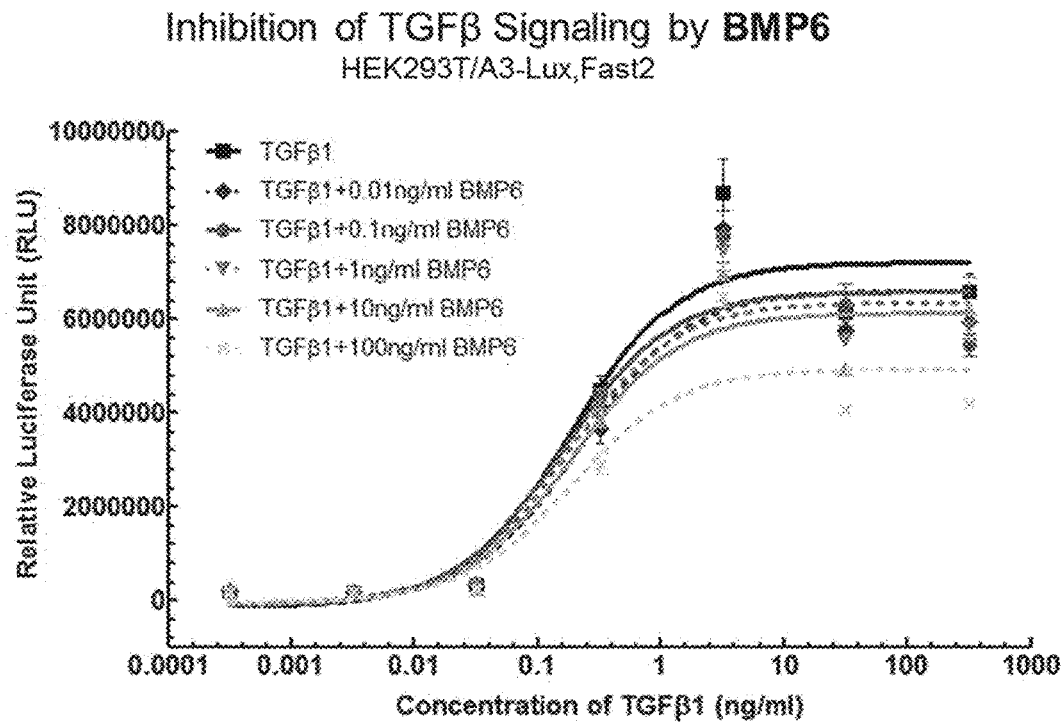
[Fig. 12]
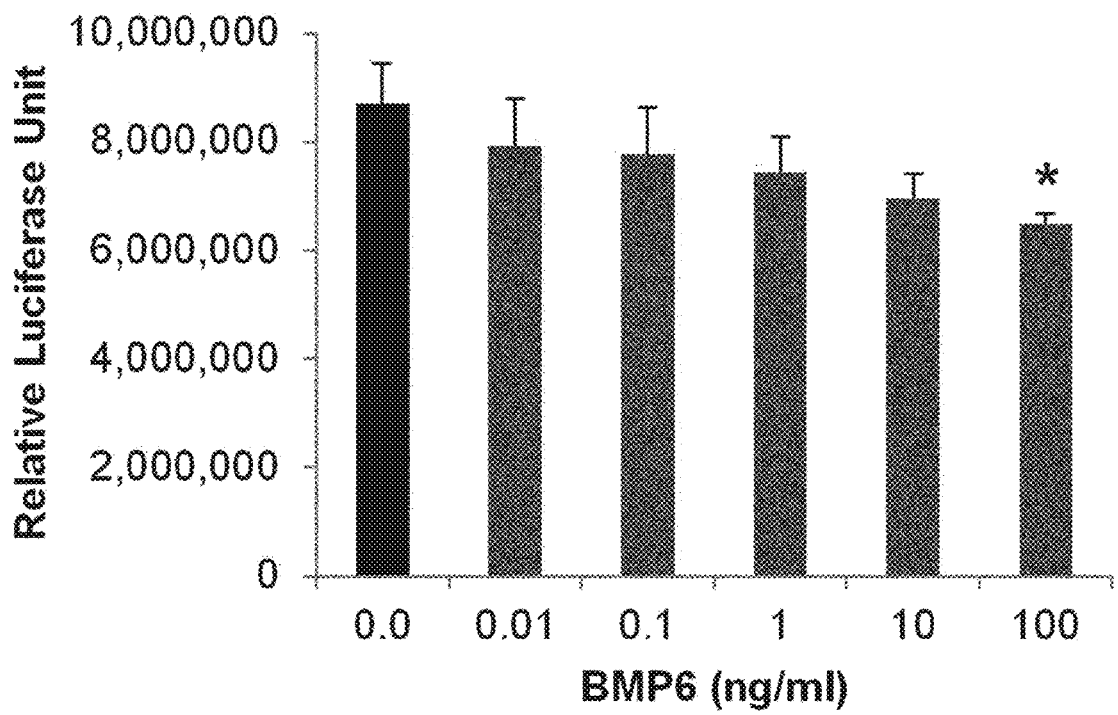

[Fig. 13]
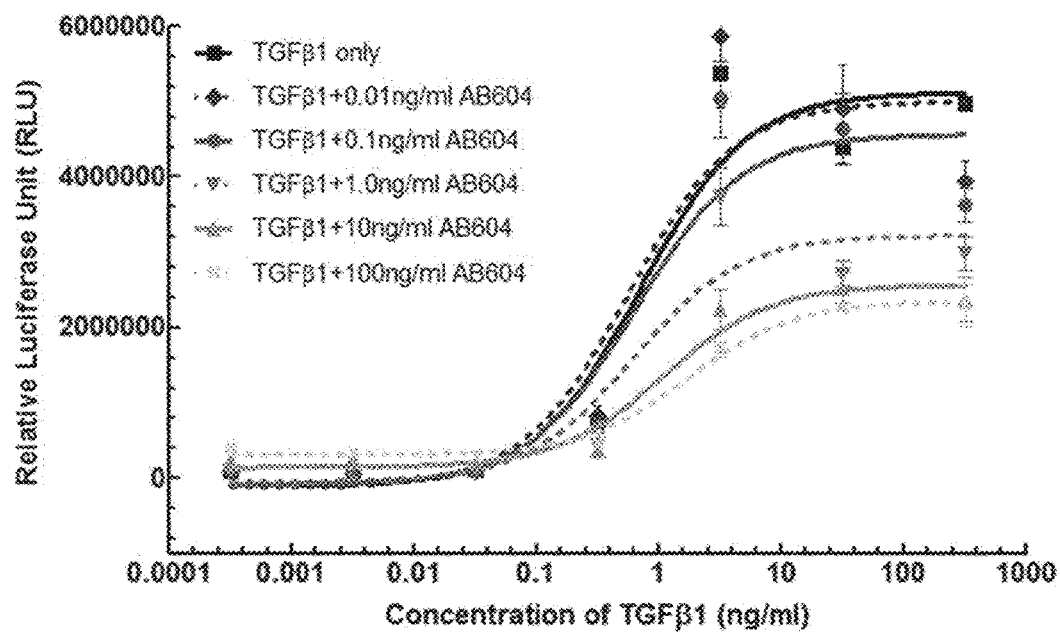
[Fig. 14]
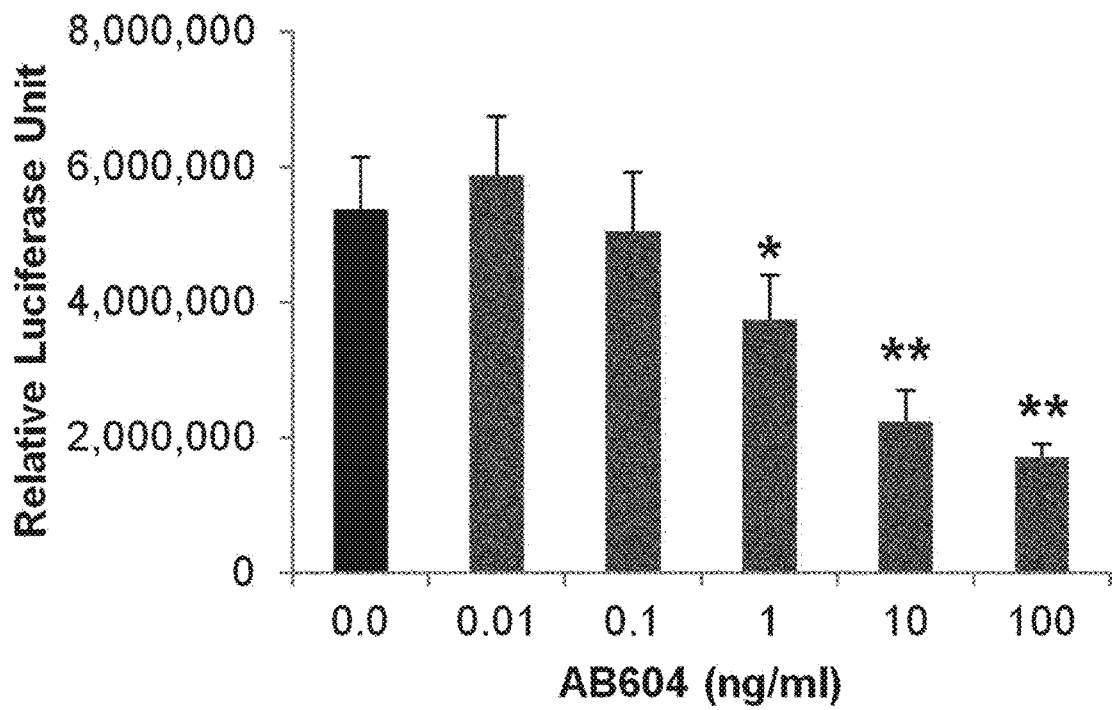

[Fig. 16]
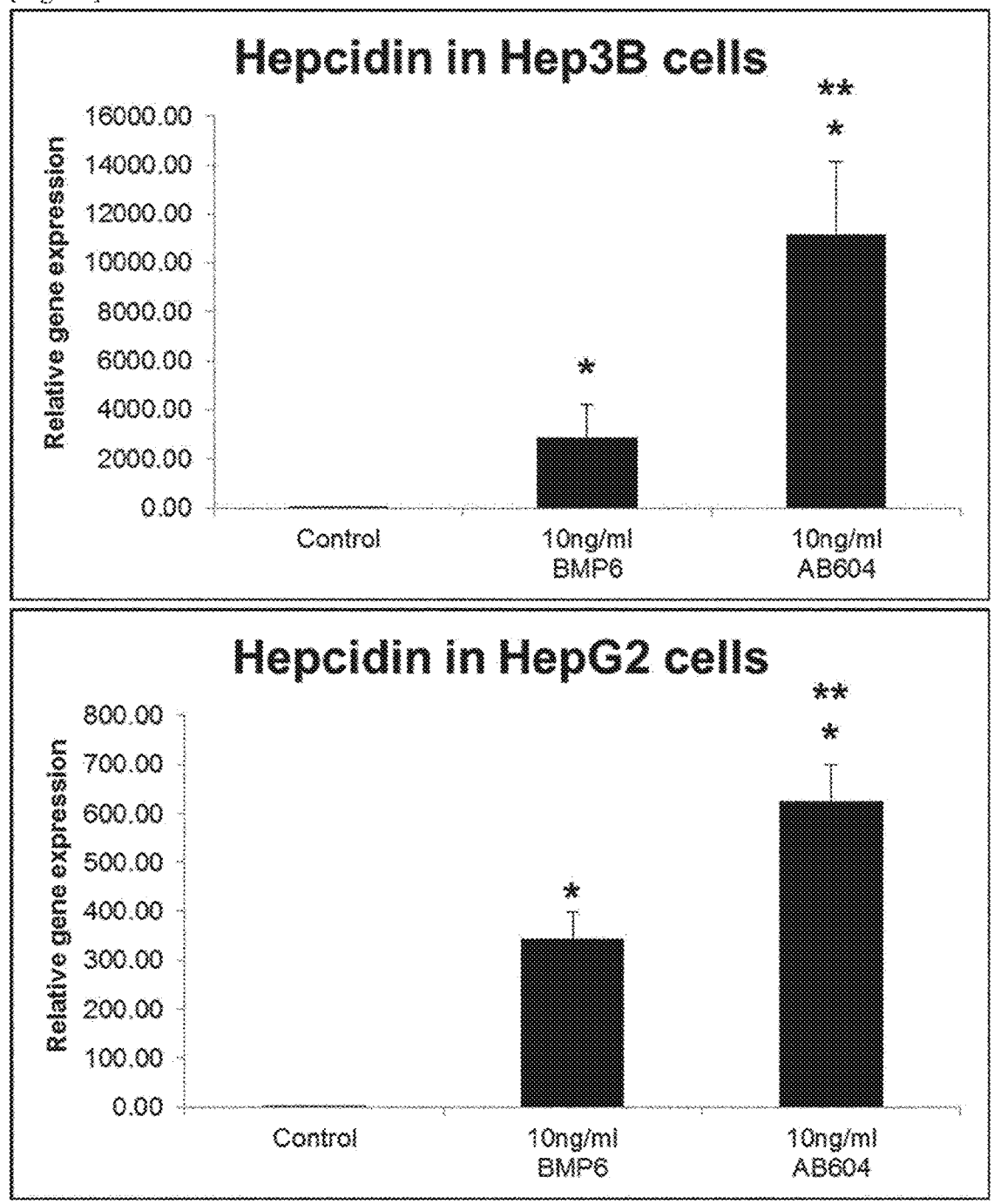
*p<0.05 versus Control, and **p<0.05 versus BMP6

[Fig. 17]
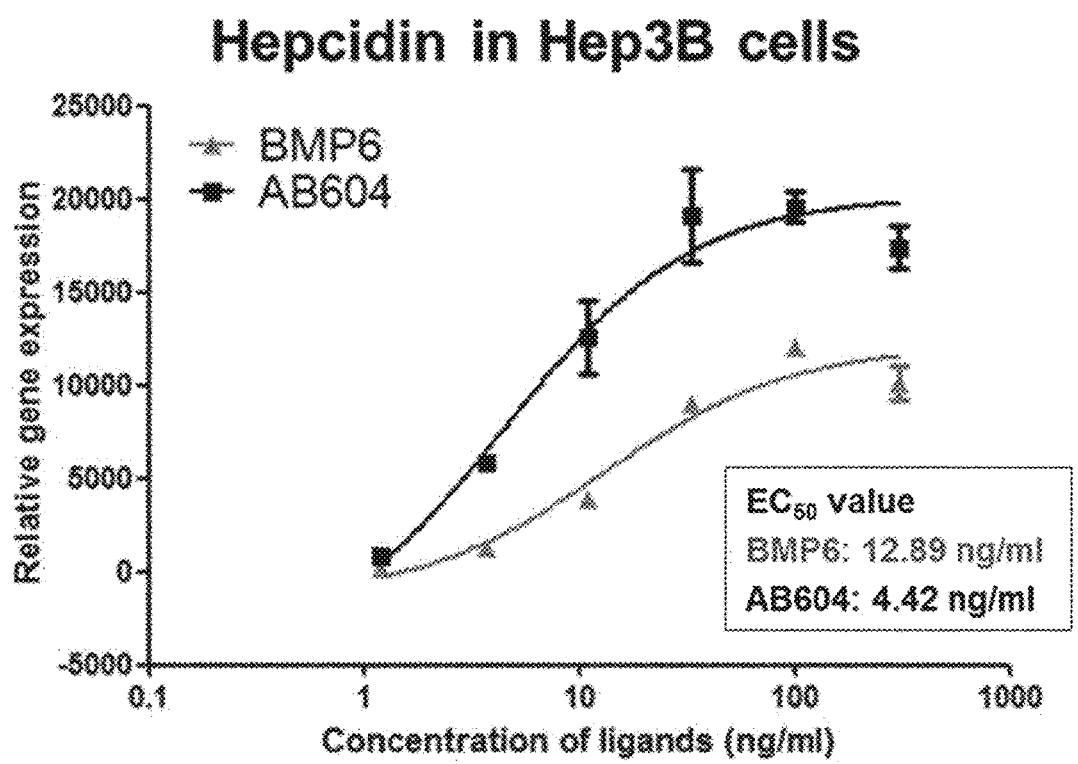

[Fig. 18]
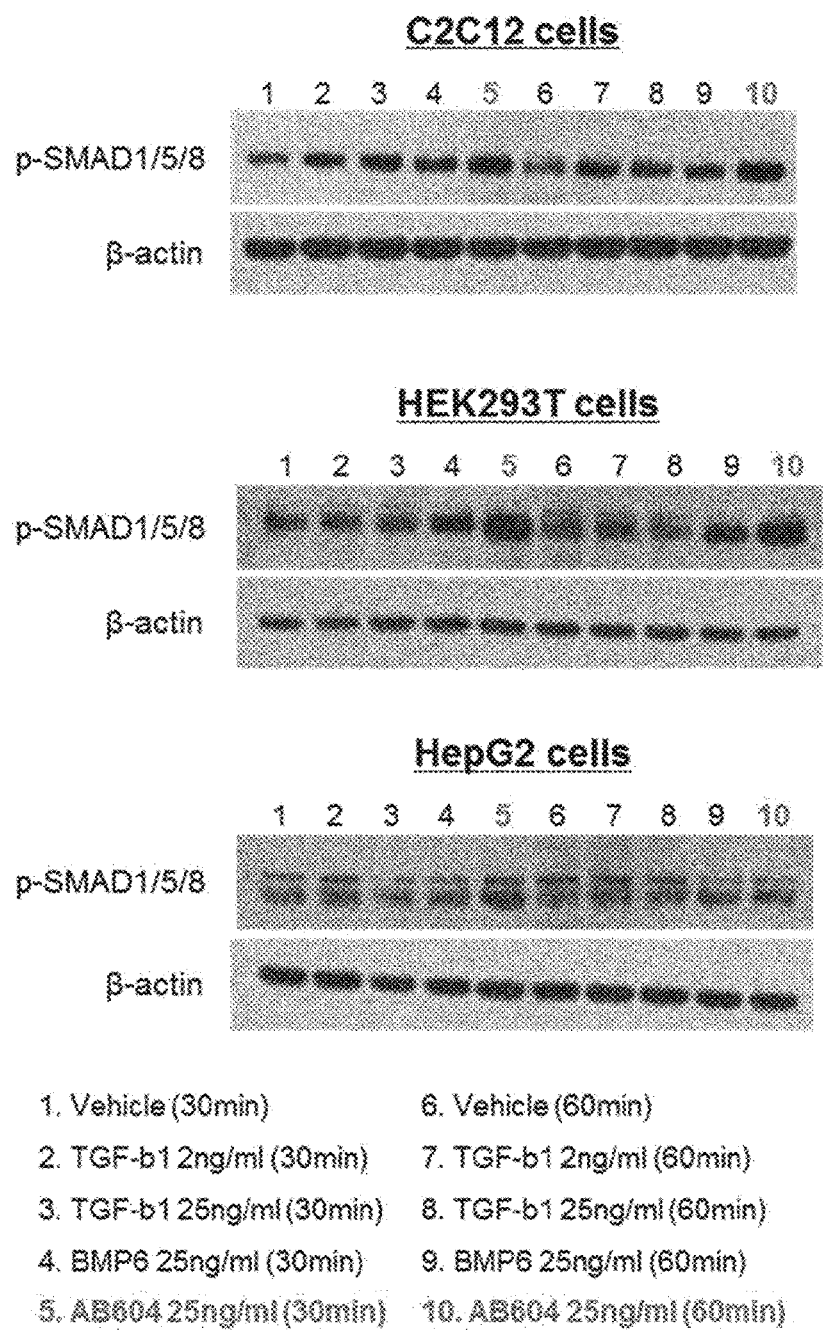

[Fig. 19]
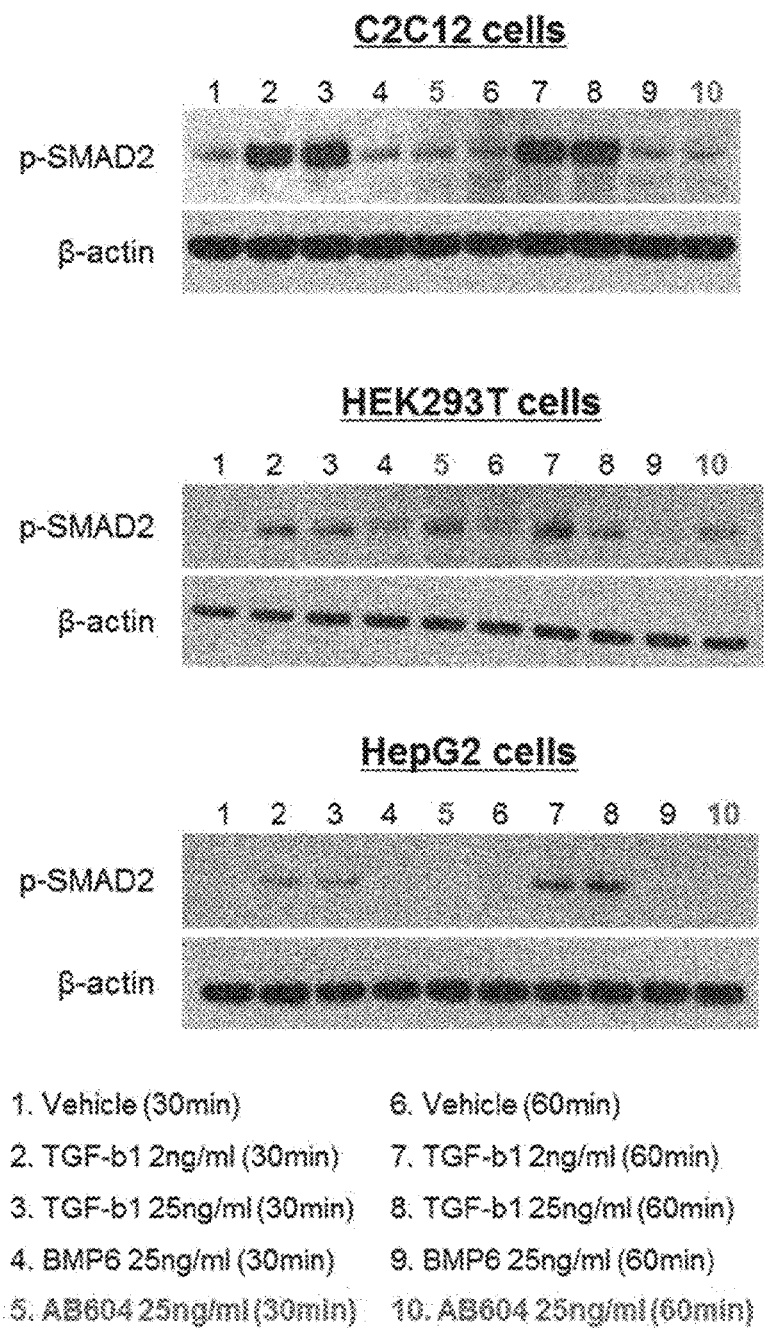

AB6 FAMILY DESIGNER LIGANDS OF TGF-β SUPERFAMILY

TECHNICAL FIELD

The present invention relates to chimeric polypeptide having TGF-beta activity, nucleic acid encoding the polypeptide, and host cell for producing the polypeptide.

BACKGROUND ART

Activins and Bone Morphogenetic Proteins (BMPs) are members of a much larger Transforming Growth Factor-beta (TGF-β) superfamily of ligands (also called TGF-β ligands). Due to their pervasiveness in numerous developmental and cellular processes, TGF-β ligands have been the focus of great interest.

DISCLOSURE OF INVENTION

Technical Problem

For TGF-β ligands to be successfully used as therapeutic tools, several hurdles need to be overcome. The ability to specifically modify and alter the properties of TGF-β ligands, as well as generate those ligands in significant quantities is required.

Solution to Problem

1. A chimeric polypeptide which has at least 95% sequence identity to an amino acid sequence comprising a first, a second, a third, a fourth, a fifth, and a sixth domains of amino acid residues, wherein the first domain of amino acid residues is selected from a group consisting of amino acid residues 1 to $X_{1b}$ of SEQ ID NO:2, amino acid residues 1 to $X_{1aa}$ of SEQ ID NO:4, amino acid residues 1 to $X_{1ab}$ of SEQ ID NO:6, amino acid residues 1 to $X_{1ac}$ of SEQ ID NO:8, and amino acid residues 1 to $X_{1ac}$ of SEQ ID NO: 10; the second domain of amino acid residues is selected from a group consisting of amino acid residues $X_{1b}$ to $X_{2b}$ of SEQ ID NO:2, amino acid residues $X_{1aa}$ to $X_{2aa}$ of SEQ ID NO:4, amino acid residues $X_{1ab}$ to $X_{2ab}$ of SEQ ID NO:6, amino acid residues $X_{1ac}$ to $X_{2ac}$ of SEQ ID NO:8, and amino acid residues $X_{1ae}$ to $X_{2ae}$ of SEQ ID NO: 10; the third domain of amino acid residues is selected from a group consisting of amino acid residues $X_{2b}$ to $X_{3b}$ of SEQ ID NO:2, amino acid residues $X_{2aa}$ to $X_{3aa}$ of SEQ ID NO:4, amino acid residues $X_{2ab}$ to $X_{3ab}$ of SEQ ID NO:6, amino acid residues $X_{2ac}$ to $X_{3ac}$ of SEQ ID NO:8, and amino acid residues $X_{2ae}$ to $X_{3ae}$ of SEQ ID NO: 10; the fourth domain of amino acid residues is selected from a group consisting of amino acid residues $X_{3b}$ to $X_{4b}$ of SEQ ID NO:2, amino acid residues $X_{3aa}$ to $X_{4aa}$ of SEQ ID NO:4, amino acid residues $X_{3ab}$ to $X_{4ab}$ of SEQ ID NO:6, amino acid residues $X_{3ac}$ to $X_{4ac}$ of SEQ ID NO:8, and amino acid residues $X_{3ae}$ to $X_{4ae}$ of SEQ ID NO: 10; the fifth domain of amino acid residues is selected from a group consisting of amino acid residues $X_{4ab}$ to $X_{5b}$ of SEQ ID NO:2, amino acid residues $X_{4aa}$ to $X_{5aa}$ of SEQ ID NO:4, amino acid residues $X_{4ab}$ to $X_{5ab}$ of SEQ ID NO:6, amino acid residues $X_{4ac}$ to $X_{5ac}$ of SEQ ID NO:8, and amino acid residues $X_{4ae}$ to $X_{5ae}$ of SEQ ID NO: 10; and the sixth domain of amino acid residues is selected from a group consisting of amino acid residues $X_{5b}$ to $X_{6b}$ of SEQ ID NO:2, amino acid residues $X_{5aa}$ to $X_{6aa}$ of SEQ ID NO:4, amino acid residues $X_{5ab}$ to $X_{6ab}$ of SEQ ID NO:6, amino acid residues $X_{5ac}$ to $X_{6ae}$ of SEQ ID NO:8, and amino acid residues $X_{5ac}$ to $X_{6ae}$ of SEQ ID NO: 10; wherein $X_{1b}$ is 43, 44, 45, 46, 47, 48, 49, 50, 51, or 52; $X_{2b}$ is 61, 62, 63, 64, 65, 66, 67, 68, 69, or 70; $X_{3b}$ is 75, 76, 77, 78, 79, 80, 81, 82, 83, 84, 85, 86, 87, or 88; $X_{4b}$ is 95, 96, 97, 98, 99, 100, 101, 102, or 103; $X_{5b}$ is 107, 108, 109, 110, 111, 112, 113, 114, or 115; $X_{6b}$ is 130, 131, or 132; $X_{1aa}$ is 22, 23, 24, 25, 26, 27, 28, 29, 30, or 31; $X_{2aa}$ is 41, 42, 43, 44, 45, 46, 47, 48, 49, 50, or 51; $X_{3aa}$ is 55, 51, 52, 53.54, 55, 56, 57, 58, 59, 60, 61, 62, 63, 64, 65, 66, 67, 68, 69, 70, 71, 72, 73, or 74; $X_{4aa}$ is 79, 80, 81, 82, 83, 84, 85, 86, or 87; $X_{5aa}$ is 91, 92, 93, 94, 95, 96, 97, 98, 99, or 100; $X_{6aa}$ is 114, 115, or 116; $X_{1ab}$ is 22, 23, 24, 25, 26, 27, 28, 29, 30, or 31; $X_{2ab}$ is 41, 42, 43, 44, 45, 46, 47, 48, 49, 50, or 51; $X_{3ab}$ is 55, 51, 52, 53, 54, 55, 56, 57, 58, 59, 60, 61, 62, 63, 64, 65, 66, 67, 68, 69, 70, 71, 72, 73, or 74; $X_{4ab}$ is 78, 79, 80, 81, 82, 83, 84, 85, or 86; $X_{5ab}$ is 90, 91, 92, 93, 94, 95, 96, 97, 98, or 99; $X_{6ab}$ is 113, 114, or 115; $X_{1ac}$ is 22, 23, 24, 25, 26, 27, 28, 29, 30, or 31; $X_{2ac}$ is 41, 42, 43, 44, 45, 46, 47, 48, 49, 50, or 51; $X_{3ac}$ is 55, 51, 52, 53, 54, 55, 56, 57, 58, 59, 60, 61, 62, 63, 64, 65, 66, 67, 68, 69, 70, 71, 72, 73, or 74; $X_{4ac}$ is 79, 80, 81, 82, 83, 84, 85, 86, or 87; $X_{5ac}$ is 91, 92, 93, 94, 95, 96, 97, 98, 99, or 100; $X_{6ac}$ is 114, 115, or 116; $X_{1ae}$ is 22, 23, 24, 25, 26, 27, 28, 29, 30, or 31; $X_{2ae}$ is 41, 42, 43, 44, 45, 46, 47, 48, 49, 50, or 51; $X_{3ae}$ is 55, 51, 52, 53, 54, 55, 56, 57, 58, 59, 60, 61, 62, 63, 64, 65, 66, 67, 68, 69, 70, 71, 72, 73, or 74; $X_{4ae}$ is 77, 78, 79, 80, 81, 82, 83, 84, or 85; $X_{5ae}$ is 89, 90, 91, 92, 93, 94, 95, 96, 97, or 98; and $X_{6ae}$ is 112, 113, or 114; and wherein the chimeric polypeptide is capable of binding to one or more of Transforming Growth Factor-beta (TGF-β) superfamily members; or one or more of TGF-β receptors.

2. The chimeric polypeptide of as set forth in 1, wherein the sequence of said polypeptide is described by an algorithm 1n2n3n4n5n6n, wherein said 1n, 2n, 3n, 4n, 5n, and 6n represent respectively the first, second, third, fourth, fifth, and sixth domain; and said n is either a or b, and wherein said a represents an amino acid sequence derived from the sequence of SEQ ID NO:2; and said b represents an amino acid sequence derived from any one selected from the group consisting of SEQ ID NO:4, SEQ ID NO:6, SEQ ID NO:8, and SEQ ID NO: 10.

3. The chimeric polypeptide of as set forth in 2, wherein the sequence of said polypeptide is described by an algorithm 1b2a3b4b5a6a.

4. The chimeric polypeptide of as set forth in 1, wherein said first domain comprises amino acid residues 1 to 47 of SEQ ID NO:2; said second domain comprises amino acid residues 28 to 45 of SEQ ID NO:4; said third domain comprises amino acid residues 66 to 85 of SEQ ID NO:2; said fourth domain comprises amino acid residues 86 to 99 of SEQ ID NO:2; said fifth domain comprises amino acid residues 84 to 95 of SEQ ID NO:4; and said sixth domain comprises amino acid residues 96 to 116 of SEQ ID NO:4.

5. The chimeric polypeptide of as set forth in 1, wherein said polypeptide comprises the sequence as set forth in SEQ ID NO: 12.

6. The chimeric polypeptide of as set forth in 1, wherein said polypeptide has at least 95% sequence identity to the sequence as set forth in SEQ ID NO: 12.

7. The chimeric polypeptide of as set forth in 1, wherein said chimeric polypeptide has at least 97% sequence identity to the amino acid sequence comprising said first domain, said second domain, said third domain, said fourth domain, said fifth domain, and said sixth domain.

8. A homo-dimer of the chimeric polypeptide of as set forth in 1, 2, 3, 4, 5, 6, or 7.

9. A hetero-dimer of the chimeric polypeptide of as set forth in 1, 2, 3, 4, 5, 6, or 7.

Advantageous Effects of Invention

The chimeric polypeptide of an embodiment can refold efficiently and can be produced at a high yield.

The chimeric polypeptide of an embodiment alone or in combination with a pharmaceutically acceptable carrier can be used to treat a liver disease.

The chimeric polypeptide of an embodiment alone or in combination with a pharmaceutically acceptable carrier can be used to treat a bone and cartilage disease.

BRIEF DESCRIPTION OF DRAWINGS

FIG. 1 shows the strategies used in an embodiment for generating activin/BMP-6 chimeras, such as AB604, using domains from two different ligands in TGF-beta superfamily.

FIG. 2 shows sequence comparison of TGF-beta superfamily members.

FIG. 3 shows refolding efficiency of BMP-2, 3, 6 and 7.

FIG. 4 shows regions with sequence identity between BMP-6 and Activin which were identified as putative crossover points.

FIG. 5 shows amino acid sequence of AB604.

FIG. 6 shows SDS-PAGE gel of AB604 showing that AB604 exists as monomers in the inclusion bodies.

FIG. 7 shows reducing and non-reducing SDS-PAGE showing that purified activin/BMP-6 chimeras were disulfide-bonded dimers.

FIG. 8 shows comparison of Smad-1 signaling activity of AB604, BMP-2 and BMP-6.

FIG. 9 shows comparison of Smad-1 signaling activity of AB604 and AB204

FIG. 10 shows Smad-2 signaling activity of AB604.

FIG. 11 shows inhibition of signaling activity of TGFβ1 by BMP6.

FIG. 12 shows inhibition of signaling activity of TGFβ1 by BMP6 in the presence of 3.0 ng/ml of TGFβ1.

FIG. 13 shows inhibition of signaling activity of TGFβ1 by AB604.

FIG. 14 shows inhibition of signaling activity of TGFβ1 by AB604 in the presence of 3.0 ng/ml of TGFβ1.

FIG. 16 shows comparison of hepcidin expression regulation by BMP6 and AB604.

FIG. 17 shows comparison of dose-dependent profile of hepcidin gene expression by BMP6 and AB604.

FIG. 18 shows comparison of SMAD1/5/8 phosphorylation by AB604, TGFβ1 and BMP6.

FIG. 19 shows comparison of SMAD2 phosphorylation by AB604, TGFβ1 and BMP6.

BEST MODE FOR CARRYING OUT THE INVENTION

Figure 15A:
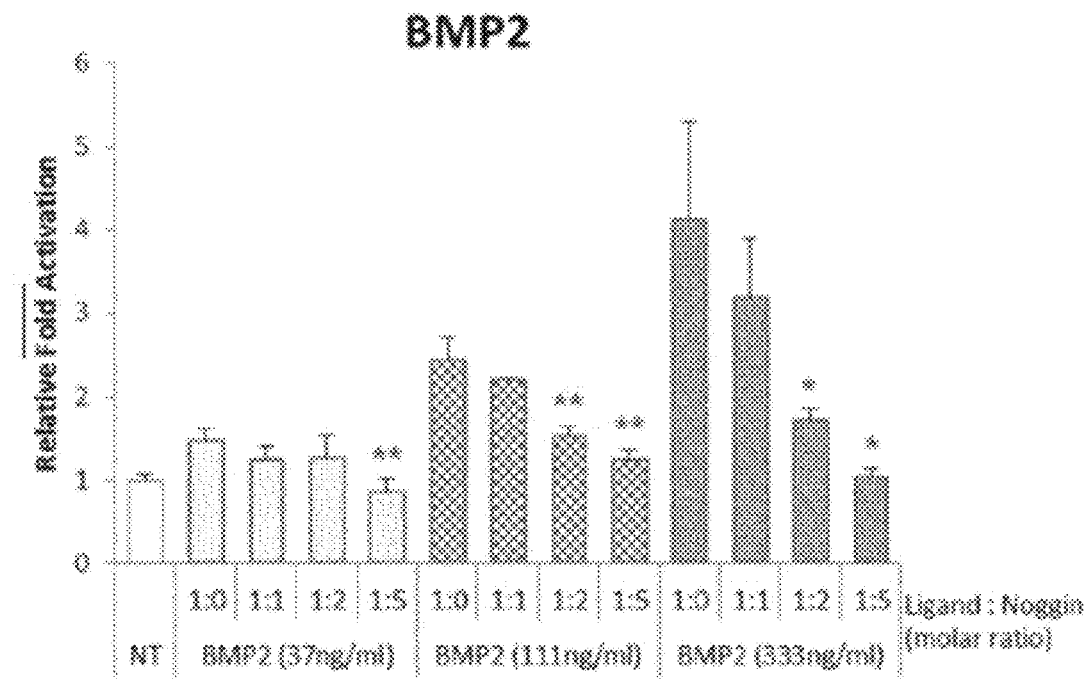
FIG. 15 shows suppression of BMP2, BMP6, or AB604 activity by noggin.

An embodiment provides a non-naturally occurring chimeric polypeptide having an activity provided by a TGF-beta family member. The chimeric polypeptide of an embodiment comprises two or more domains or fragments from parental TGF-beta proteins operably linked such that the resulting polypeptide is capable of modulating a pathway associated with a TGF-beta family member. In one embodiment, the pathway is a SMAD pathway or a DAXX (Death-associated protein 6) pathway.

An embodiment of the invention provides designer TGF-beta ligands that can be synthesized by selecting and conjoining different domains of TGF-beta superfamily ligands to construct new ligands (i.e. designer ligands). These novel chimeric ligands possess entirely new protein sequence library that differs from naturally existing TGF-beta superfamily ligands. This approach originates primarily from the recognition of the structural commonality among natural TGF-beta superfamily ligands. All ~40 TGF-beta superfamily ligands share the same overall architecture with generic characteristics for each region of the protein. The framework of TGF-beta ligands can be divided into (generally) six domains that all superfamily members share.

An embodiment of the invention provides a chimeric polypeptide comprising: at least two domains, a first domain of the polypeptide comprising a sequence having at least 80% identity to a first TGF-beta family protein and a second domain comprising a sequence having at least 80% identity to a second TGF-beta family protein, wherein the domains are operably linked and have activity of at least one of the first or second parental TGF-beta family protein. In one embodiment, the chimeric polypeptide comprises 6 domains operably linked N-terminus to C-terminus. In one embodiment, each of the first and second TGF-beta family proteins has structural similarity and each domain corresponds to a structural motif. In one embodiment, the first TGF-beta family protein is BMP-6 and the second TGF-beta family protein is activin. In one embodiment, the polypeptide comprises an N-terminal domain from BMP-6.

In one embodiment, the domains of BMP-6, activin-βA, activin-βB, activin-βC, and activin-βE are as described in Table 1, wherein the chimeric polypeptide has an order of domain 1-domain 2-domain 3-domain 4-domain 5-domain 6, from the N-terminal to the C-terminal orientation.

An embodiment of the invention provides a chimeric polypeptide comprising at least 80%, 81%, 82%, 83%, 84%, 85%, 86%, 86%, 87%, 88%, 89%, 90%, 91%, 92%, 93%, 94%, 95%, 96%, 97%, 98%, 99% or more identity to a sequence as set forth in SEQ ID NO: 12 and wherein the polypeptide modulates the SMAD or DAXX pathway.

An embodiment of the invention provides a chimeric TGF-beta family polypeptide comprising a domain of a first TGF-beta family protein operably linked to a domain of a second different TGF-beta family protein to provide a chimeric polypeptide having SMAD or DAXX modulating activity. In one embodiment, the chimeric TGF-beta family polypeptide comprises at least 80%, 81%, 82%, 83%, 84%, 85%, 86%, 86%, 87%, 88%, 89%, 90%, 91%, 92%, 93%, 94%, 95%, 96%, 97%, 98%, 99% or more identity to the sequence as set forth in SEQ ID NO: 12 and wherein the polypeptide modulates the SMAD or DAXX pathway.

An embodiment of the invention provides a polynucleotide encoding a polypeptide of an embodiment. In one embodiment, the polynucleotide has at least 80%, 81%, 82%, 83%, 84%, 85%, 86%, 86%, 87%, 88%, 89%, 90%, 91%, 92%, 93%, 94%, 95%, 96%, 97%98%, 99% or more identity to a sequence as set forth in SEQ ID NO: 11. A vector comprising such polynucleotide is also provided along with a recombinant cell.

An embodiment of the invention provides novel ligands of the TGF-beta superfamily, wherein each of the ligands is a chimeric protein with at least one of six domains from a foreign or different member of the TGF-beta superfamily.

As used herein and in the appended claims, the singular forms "a," "and," and "the" include plural referents unless the context clearly dictates otherwise. Thus, for example, reference to "a domain" includes a plurality of such domains and reference to "the protein" includes reference to one or more proteins, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Although methods and materials similar or equivalent to those described herein can be used in the practice of the disclosed methods and compositions, the exemplary methods and materials are described herein.

Unless defined otherwise, all technical and scientific terms used herein have the same meaning as commonly understood to one of ordinary skill in the art to which this disclosure belongs. Thus, as used throughout the instant application, the following terms shall have the following meanings.

"Amino acid" is a molecule having the structure wherein a central carbon atom (the alpha-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

"Protein" or "polypeptide" refers to any polymer of two or more individual amino acids (whether or not naturally occurring) linked via a peptide bond, and occurs when the carboxyl carbon atom of the carboxylic acid group bonded to the alpha-carbon of one amino acid (or amino acid residue) becomes covalently bound to the amino nitrogen atom of amino group bonded to the carbon of an adjacent amino acid. The term "protein" is understood to include the terms "polypeptide" and "peptide" (which, at times may be used interchangeably herein) within its meaning. In addition, proteins comprising multiple polypeptide subunits (e.g., DNA polymerase ill, RNA polymerase 11) or other components (for example, an RNA molecule, as occurs in telomerase) will also be understood to be included within the meaning of "protein" as used herein. Similarly, fragments of proteins and polypeptides are also within the scope of the present invention and may be referred to herein as "proteins." In one aspect of an embodiment, a polypeptide comprises a chimera of two or more parental domains.

As used herein, TGF-beta superfamily member refers to a TGF-beta superfamily (including bone morphogenic factors) gene or protein of any species, particularly a mammalian species, including but not limited to bovine, ovine, porcine, murine, equine, and human. "TGF-beta superfamily polypeptide" refers to the amino acid sequences of purified TGF-beta superfamily protein obtained from any species, particularly a mammalian species, including bovine, ovine, porcine, murine, equine, and human and from any source, whether natural, synthetic, semi-synthetic, or recombinant.

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

"Fused," "operably linked," and "operably associated" are used interchangeably herein to broadly refer to a chemical or physical coupling of two otherwise distinct domains, wherein each domain has independent biological function. As such, an embodiment of the invention provides TGF-beta (e.g., BMP-6 or activin) domains that are fused to one another such that they function as a polypeptide having a TGF-beta family activity or an improvement or change in ligand specificity of a TGF-beta family of polypeptides. In one embodiment, a chimeric polypeptide comprising a plurality of domains from two parental TGF-beta family polypeptides are linked such that they are part of the same coding sequence, each domain encoded by a polynucleotide from a parental TGF-beta family polypeptide, wherein the polynucleotide is in frame such that the polynucleotide when transcribed encodes a single mRNA that when translated comprises a plurality of domains as a single polypeptide. Typically, the coding domains will be linked "in-frame" either directly or separated by a peptide linker and encoded by a single polynucleotide. Various coding sequences for peptide linkers and peptide are known in the art.

"Polynucleotide" or "nucleic acid" refers to a polymeric form of nucleotides. In some instances a polynucleotide comprises a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector, into an autonomously replicating plasmid or virus; or into the genomic DNA of a prokaryote or eukaryote, or which exists as a separate molecule (e.g., a cDNA) independent of other sequences. The nucleotides of an embodiment can be ribonucleotides, deoxyribonucleotides, or modified forms of either nucleotide. A polynucleotide as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term polynucleotide encompasses genomic DNA or RNA (depending upon the organism, i.e., RNA genome of viruses), as well as mRNA encoded by the genomic DNA, and cDNA.

"Chimera" or "chimeric protein" or "chimeric polypeptide" refers to a combination of at least two domains of at least two different parent proteins. For example, a chimeric BMP will have at least two domains from two different parent BMPs; or BMP and other member of the TGF-beta superfamily (for example, activins), or alternatively, an unrelated protein. A chimeric protein may also be an "interspecies," "intergenic," etc. fusion of protein structures (the same or different member protein) expressed by different kinds of organisms. In one embodiment, two domains are connected so as to result in a new chimeric protein. In other words, a protein will not be a chimera if it has the identical sequence of either one of the full-length parents. A chimeric protein can comprise more than two domains from two different parent proteins. For example, there may be 2, 3, 4, 5, 6 or 10-20, or more parents from which the domains may be derived in generating a final chimera or library of chimeras. The domain of each parent protein can be very short or very long, the domains can range in length of contiguous amino acids from 1 to about the full length of the protein. In one embodiment, the minimum length is 5 amino acids. Generally, the domain, is one of six domains, alternatively five domains (see FIG. 2).

The six domains of a TGF-beta superfamily member are identified based on the structural architecture of the member protein and/or the primary amino acid sequence as aligned against other homologous member proteins. As identified, the member protein is generally divided into 6 distinct domains (although, alternatively, 5 distinct domains) based on domains derived to minimize alterations, or alternatively viewed, maximize alterations, to the aligned native TGF-beta member sequence during chimera engineering. Generally, FIG. 2 shows the relative positions of the distinct domains overlapping the aligned sequences of each of several TGF-beta superfamily members. The vertical line denotes a general position for cross-over between domains in generating the chimera. The amino acids that can overlap the two domains can be defined as being plus or minus about 5 amino acids (or alternatively, 8, 7, 6, 5, 4, 3, 2 or 1 amino acids) in either direction of the vertical line. Also in FIG. 2 is shown a boxed set of amino acids that identify additional junctions that can be used to generate chimera. The J1-J5 junctions are positions general conservation across the TGF-beta family proteins that can be used to generate cross-over points.

Although relatively distinct, the domains may comprise a particular amino acid sequence or an original amino acid sequence that is amenable to substitution(s), insertion(s), additional amino acid(s) at either or both termini of the original sequence, or other modifications. By "amenable", it is meant that the structural integrity of each domain is maintained as compared to the domain of the original sequence. For example, a domain described herein of a TGF-beta superfamily member may shift by 10, 5, 3, 2, or 1, or preferably no more than 1 amino acid on either or both termini of domain as identified. An embodiment of the invention provides a chimeric protein comprising a fusion of at least one domain from a TGF-beta member with a second domain from a second TGF-beta member, wherein the first domain is foreign to the second TGF-beta member. Utilizing the five-six domains on a single subunit of the TGF-beta superfamily ligand as a scaffold framework, new (designer) sequences can be recombinantly linked by mixing domains from different TGF-beta ligands in the same order as they appear in nature. This assembly produces new sequences that are partly similar to one of several different target sequences, but distinctly different from any naturally occurring sequences.

In one embodiment, a single crossover point is defined for the amino acid sequences of two parents. The crossover location defines where one parent's domain will stop and where the next parent's domain will start. Thus, a simple chimera would only have one crossover location where the domain before that crossover location would belong to one parent and the domain after that crossover location would belong to the second parent. In one embodiment, the chimera has more than one crossover location. For example, 2, 3, 4, 5, 6, 7, 8, 9, 10, 11-30, or more crossover locations. In one embodiment, the parental strands are defined as having 1, 2, 3, 4 or 5 crossover locations. How these crossover locations are named and defined are both discussed below. In an embodiment where there are two crossover locations and two parents, there will be a first contiguous domain from a first parent, followed by a second contiguous domain from a second parent, followed by a third contiguous domain from the first parent. Contiguous is meant to denote that there is nothing of significance interrupting the domains. These contiguous domains are connected to form a contiguous amino acid sequence. For example, an activin/BMP-6 chimera derived from a BMP-6 wild-type parental strand and an activin wild-type parental strand with five crossovers would comprise a first domain from either BMP-6 or activin, a second domain from the opposite parental strand compared to the first domain operably linked to the first domain and comprising a structural motif downstream of the first domain, a third domain from the opposite parental strand compared to the second domain operably linked to the second domain and comprising a structural motif downstream of the second domain, a fourth domain from the opposite parental strand compared to the third domain operably linked to the third domain and comprising a structural motif downstream of the third domain, a fifth domain from the opposite parental strand compared to the fourth domain operably linked to the fourth domain and comprising a structural motif downstream of the fourth domain, and a sixth domain from the opposite parental strand compared to the fifth domain operably linked to the fifth domain and comprising a structural motif downstream of the fifth domain, all connected in one contiguous amino acid chain.

As appreciated by one of skill in the art, variants of chimeras exist as well as the exact sequences. In other words conservative amino acid substitutions may be incorporated into the chimera (e.g., from about 1-10 conservative amino acid substitutions). Thus, not 100% of each domain need be present in the final chimera if it is a variant chimera. The amount that may be altered, either through additional residues or removal or alteration of residues will be defined as the term variant is defined. Of course, as understood by one of skill in the art, the above discussion applies not only to amino acids but also nucleic acids which encode for the amino acids.

"Conservative amino acid substitution" refers to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, isoleucine, and methionine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine, arginine, and histidine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Reference sequence" refers to a defined sequence used as a basis for a sequence comparison. A reference sequence may be a subset of a larger sequence, for example, a domain of a full-length gene or polypeptide sequence. Generally, a reference sequence can be at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity.

"Sequence identity" means that two amino acid sequences are substantially identical (i.e., on an amino acid-by-amino acid basis) over a window of comparison. The term "sequence similarity" refers to similar amino acids that share the same biophysical characteristics. The term "percentage of sequence identity" or "percentage of sequence similarity" is calculated by comparing two optimally aligned sequences over the window of comparison, determining the number of positions at which the identical residues (or similar residues) occur in both polypeptide sequences to yield the number of matched positions, dividing the number of matched positions by the total number of positions in the window of comparison (i.e., the window size), and multiplying the result by 100 to yield the percentage of sequence identity (or percentage of sequence similarity). With regard to polynucleotide sequences, the terms sequence identity and sequence similarity have comparable meaning as described for protein sequences, with the term "percentage of sequence identity" indicating that two polynucleotide sequences are identical (on a nucleotide-by-nucleotide basis) over a window of comparison. As such, a percentage of polynucleotide sequence identity (or percentage of polynucleotide sequence similarity, e.g., for silent substitutions or other substitutions, based upon the analysis algorithm) also can be calculated. Maximum correspondence can be determined by using one of the sequence algorithms described herein (or other algorithms available to those of ordinary skill in the art) or by visual inspection.

As applied to polypeptides, the term substantial identity or substantial similarity means that two peptide sequences, when optimally aligned, such as by the programs BLAST, GAP or BESTFIT using default gap weights or by visual inspection, share sequence identity or sequence similarity. Similarly, as applied in the context of two nucleic acids, the term substantial identity or substantial similarity means that the two nucleic acid sequences, when optimally aligned, such as by the programs BLAST, GAP or BESTFIT using default gap weights (described in detail below) or by visual inspection, share sequence identity or sequence similarity.

One example of an algorithm that is suitable for determining percent sequence identity or sequence similarity is the FASTA algorithm, which is described in Pearson, W. R. & Lipman, D. J., (1988) Proc. Natl. Acad. Sci. USA 85:2444. See also, W. R. Pearson, (1996) Methods Enzymology 266:227-258. Preferred parameters used in a FASTA alignment of DNA sequences to calculate percent identity or percent similarity are optimized, BL50 Matrix 15: 5, k-tuple=2; joining penalty=40, optimization=28; gap penalty 12, gap length penalty=2; and width=16.

Another example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle, (1987) J. Mol. Evol. 35:351-360. The method used is similar to the method described by Higgins & Sharp, CABIOS 5:151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is nm by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al., (1984) Nuc. Acids Res. 12:387-395).

Another example of an algorithm that is suitable for multiple DNA and amino acid sequence alignments is the CLUSTALW program (Thompson, J. D. et al., (1994) Nuc. Acids Res. 22:4673-4680). CLUSTALW performs multiple pairwise comparisons between groups of sequences and assembles them into a multiple alignment based on sequence identity. Gap open and Gap extension penalties were 10 and 0.05 respectively. For amino acid alignments, the BLOSUM algorithm can be used as a protein weight matrix (Henikoff and Henikoff, (1992) Proc. Natl. Acad. Sci. USA 89:10915-10919).

FIG. 2, for example, shows an alignment of a number of TGF-beta family members. One of skill in the art can readily determine from the alignment those amino acids that are conserved across the family as well as those that are not conserved.

"Functional" refers to a polypeptide which possesses either the native biological activity of the naturally-produced proteins of its type, or any specific desired activity, for example as judged by its ability to bind to ligand or cognate molecules or induce a particular biological function (e.g., stimulate muscle growth, bone growth and the like).

The Transforming Growth Factor-beta (TGF-β) superfamily of proteins is comprised of extracellular cytokines found in the vast majority of human cells. The TGF-β superfamily ligands, of which there are ~40, can be subdivided into smaller families including TGF-β, Bone Morphogenetic Proteins (BMPs), activin and inhibin, Growth and Differentiation Factors (GDFs), Nodal, Mullerian Inhibiting Substance (MIS), and Glial cell line-Derived Neurotrophic Factors (GDNFs). TGF-β superfamily members are found in a diverse range of cell types and play roles in many fundamental cellular events including dorsal/ventral patterning and left/right axis determination to bone formation and tissue repair. More recently, several TGF-β ligands have been shown to be involved in the maintenance or direct the differentiation of stem cells. Due to their pervasiveness, regulation of TGF-β ligand signaling holds promise for the treatment of a wide range of different diseases from skeletal and muscle abnormalities to numerous neoplastic events. Exemplary sequences are provided herein for various members of this family or proteins, however, one of skill in the art can easily identify homologs and variants using publicly available databases by word search or sequence BLAST searches.

There are generally recognized several subfamilies within the superfamily of TGF-beta (TGF-β1-β5) as well as the differentiation factors (e.g., Vg-1), the hormones activin and inhibin, the Mullerian inhibiting substance (MIS), osteogenic and morphogenic proteins (e.g., OP-1, OP-2, OP-3, other BMPs), the developmentally regulated protein Vgr-1, the growth/differentiation factors (e.g., GDF-1, GDF-3, GDF-9 and dorsalin-1), etc. See, e.g., Spam and Roberts (1990) in Peptide Growth Factors and Their Receptors, Spom and Roberts, eds., Springer-Verlag: Berlin pp. 419-472; Weeks and Melton (1987) Cell 51: 861-867; Padgett et al. (1987) Nature 325: 81-84; Mason et al. (1985) Nature 318: 659-663; Mason et al. (1987) Growth Factors 1: 77-88; Cate et al. (1986) Cell 45: 685-698; PCT/US90/05903; PCT/US91/07654; PCT/WO94/10202; U.S. Pat. Nos. 4,877, 864; 5,141,905; 5,013,649; 5,116,738; 5,108,922; 5,106, 748; and 5,155,058; Lyons et al. (1989) Proc. Natl. Acad. Sci. USA 86: 4554-58; McPherron et al. (1993) J. Biol. Chem. 268: 3444-3449; Easier et al. (1993) Cell 73: 687-702.

Morphogenic proteins of the TGF-beta superfamily include the mammalian osteogenic protein-1 (OP-1, also known as BMP-7), osteogenic protein-2 (OP-2, also known as BMP-8), osteogenic protein-3 (053). BMP-2 (also known as BMP-2A or CBMP-2A, and the *Drosophila* homolog DPP), BMP-3, BMP-4 (also known as BMP26 or CBMP-2B). BMP-5, BMP-6 and its murine homolog Vgr-1, BMP-9, BMP-10, BMP-11, BMP-12, GDF3 (also known as Vgr2), GDF-8, GDF-9, GDF-10. GDF-11, GDF-12, BMP-13, BMP-14, BMP-15, GDF-5 (also known as CDMP-1 or MP52), GDF-6 (also known as CDMP-2 or BMP13), GDF-7 (also known as CDMP-3 or BMP-12), the *Xenopus* homolog Vg1 and NODAL, UNIVIN, SCREW, ADMP, NEURAL, etc.

TGF-β ligands are synthesized as inactive precursor molecules composed of an N-terminal pro-domain and a C-terminal mature domain linked by a protease cleavage site. To be become active, the mature domain must be cleaved from the pro-domain, commonly by a convertase, such as furin. Members of the TGF-β superfamily are classified together due to the conserved structural architecture found in their mature domains. In general, each mature ligand monomer contains 7 cysteines, 6 of which form three intra-disulfide bonds arranged in a 'cysteine knot' motif. Stretching outward from the 'cysteine knot' are 4 beta strands, creating 2 curved fingers. The last remaining cysteine forms an inter-disulfide bond with a second ligand monomer, generating a covalently linked dimer. The dimer has the overall appearance of a butterfly with the 'cysteine knot' as the body and the fingers spreading out like wings. The functional subunit for the TGF-β superfamily is the dimer and they been shown to exist both as homo- and heterodimers in vivo. Some family members, such as GDF-9 and BMP-15, lack the cysteine required to form the inter-disulfide bond yet they are still able to form stable dimers.

To initiate the signaling process, TGF-β dimers must recruit two sets of receptors, termed type I and type II. These receptors are serine/threonine kinases possessing an extracellular domain (ECD) ordered into a three-finger toxin fold, a single transmembrane domain, and a large intracellular kinase domain. TGF-β ligands have been shown to display preferences in their affinity for the different receptor types. Activin and Nodal exhibit high affinity for type 11 receptors, while BMP-2 and GDF-5 possess higher affinity for type 1 receptors. Following the binding of two high affinity receptors to a TGF-β ligand, two lower affinity receptors are then able to bind and join the complex. Upon binding of all four receptors to the TGF-β ligand, forming a 6-member ternary complex, the downstream signaling cascade is initialed. The constitutively active type II receptors phosphorylate the type I receptors which, in turn, bind and phosphorylate intracellular signaling molecules called Smads. The Smad molecules then are able to translocate to the nucleus and interact directly with transcriptional regulators. Multiple mechanisms are employed to closely regulate TGF-β signaling at different stages of the cascade: Extracellular antagonists, including Noggin, follistatin, and Inhibin; pseudo-receptors lacking the intracellular kinase domain, similar to BAMBI; or through intracellular molecules, such as inhibitory Smads.

TGF-β superfamily shows a high degree of promiscuity by receptors for the ligands. While there are over 40 TGF-β ligands, there are only 12 receptors (7 type I and 5 type II). Therefore, receptors must be able to interact with a multitude of different ligands. For instance, ActRII is known to bind activin and BMP-7 with high affinity, but binds BMP-2 with much lower affinity. In GDF-5, a single amino acid has been found which determines its type I receptor preference, while in BMP-3 a single point mutation was discovered which alters type II receptor affinity as well as imparting function to the ligand. An embodiment provides methods to create modified TGF-β ligands with novel receptor binding properties thereby diversifying TGF-β ligand function as well as a composition having such activity.

An embodiment demonstrates a TGF-beta signaling complex by utilizing novel ligand constructs. Using synthesized chimeric homo- or heterodimeric ligands, an embodiment provides a composition for use in dissecting the signaling of TGF-beta family proteins. Furthermore, utilizing such ligands allows a method for distinguishing contributions of two type I receptor interfaces from each other, and two type II receptor interfaced each other. The methods and compositions of an embodiment demonstrate a correlation between ligand-receptor affinity, signaling activity, and biological activity. The methods and compositions of an embodiment shed light on the mechanism and requirements of the TGF-beta superfamily signaling complex assembly. In addition the chimeric ligands provide novel polypeptides for use in treating diseases and disorders associated with TGF-β family of proteins.

An embodiment provides methods of making and using a novel chimeric TGF-β ligand which possesses the ability to be expressed and refolded using, for example, an *E. coli* or mammalian expression system. The strategies used in an embodiment for generating an activin/BMP-6 chimera, such as AB604, using domains from two different ligands in TGF-beta superfamily are summarized in FIG. 1. The chimera either mimic a specific TGF-β ligand's signaling characteristics or display unique signaling properties not seen in nature. In one embodiment, activin-βA and BMP-6 are used as templates to generate an activin/BMP-6 chimera. The activin/BMP-6 chimera of an embodiment shows 7-fold increase in Smad-1 signaling activity and 10-fold increase in refolding yield, compared to activin/BMP-2 (AB204). These superior properties of the activin/BMP-6 chimera of an embodiment could not have been anticipated before, considering that BMP-2 was believed to have the highest refolding efficiency among BMP proteins and that BMP-2 was also believed to show higher Smad-1 signaling activity compared to BMP-6, as described in Allendorph et al. Biochemistry, 2007:12238-47 (FIG. 3).

In one embodiment, two factors were considered when looking to design the domains of the chimera. First was a structural consideration. The overall TGF-β monomer fold is divided into 6 domains naturally: Beta strand 1 and 2, the pre-helix loop, alpha helix 1, and beta strand 3 and 4. The identification and characterization of these domains are further described in Example 4. An embodiment utilized chimeric structures to mimic these natural regions in the design. Thus, each domain can be indicated by 1, 2, 3, 4, 5, and 6. The second consideration was to minimize alterations to the aligned native TGF-beta member sequence during chimera engineering. Therefore, those regions with sequence identity between the 2 protein sequences were identified as putative cross-over points. These regions are suitable for the overlaps in DNA sequence for PCR strategy and will minimize any changes to the natural sequences. FIG. 4 illustrates the sequence and structure of these considerations. The regions are boxed and numbered according to their domain and are mapped onto the ligand monomer. Residue numbering in one embodiment is based on BMP-6 (SEQ ID NO:2). Thus, cross-over points in generating a chimeric polypeptide of an embodiment can be identified by identifying similar structural motifs in combination with at least 60%, 70%, 80%, 90%, 95%, 98%, 99% or 100% identity in a domain of the sequence between changes in the structural motif. Cross-overs at these regions (which may be between 3 to 20 amino acids) minimize disruption of the resulting chimeric polypeptide providing a stabilized chimera.

For example, a chimeric polypeptide comprising the algorithm 1b2a3b4b5a6a indicates 6 domains, the letter indicating the parental strand of each domain. Thus, in the example "1b2a3b4b5a6a", domain 1 is from parental strand "b" for BMP-6, domain 2 is from parental strand "a" for activin, domain 3 is from parental strand "b" for BMP-6, domain 4 is from parental strand "b" for BMP-6, domain 5 is from parental strand "a" for activin, and domain 6 is from parental strand "a" for activin.

In one embodiment, crossover between domains of BMP-6 and a second TGF-beta family protein can occur where structural similarity and sequence similarly overlap. FIG. 4 depicts such an overlap between BMP-6 and activin, wherein crossovers can be generated between about residue D42-P52, G62-S65; T82-H85; K94-T100; and S106-D112 (residue numbering is based on BMP-6 (SEQ ID NO:2)). Sequence alignment of BMP-6 and activin-βA highlight the boundaries of domains 1 through 6. Activin has the extra disulfide bond formed between two Cys.

Other methods for identifying crossover locations may be employed in the generation of the chimeric TGF-beta family polypeptide. For example, SCHEMA is a computational based method for predicting which fragments of homologous proteins can be recombined without affecting the structural integrity of the protein (see, e.g., Meyer et al., (2003) Protein Sci., 12:1686-1693). A chimera with higher stability are identifiable by determining the additive contribution of each domain to the overall stability, either by use of linear regression of sequence-stability data, or by reliance on consensus analysis of the MSAs of folded versus unfolded proteins. SCHEMA recombination ensures that the chimera retain biological function and exhibit high sequence diversity by conserving important functional residues while exchanging tolerant ones.

As presented in an embodiment, it has been found that when these recombined, functional chimeric TGF-beta family polypeptides are generated their ligand specificity can be improved or biological activity can be altered or improved compared to an unrecombined parental polypeptide. Because of differences in activity/ligand profiles, these engineered chimeric TGF-beta family polypeptides provide a unique basis to screen for activities for ligand specific activation and inhibition, provide novel therapeutic polypeptides and research reagents.

For example, in the chimera of an embodiment, domains 1, 2, 3, 4, 5, and 6 can be selected from the following sequences (TABLE 1) wherein the polypeptide comprises a structure (domain 1-domain 2-domain 3-domain 4-domain 5-domain 6):

TABLE 1

| Amino acids (Domain #) | Parental SEQ ID NO: | Variable definition |
|---|---|---|
| 1-$X_{1b}$ (1) | 2 | $X_{1b}$ is 43, 44, 45, 46, 47, 48, 49, 50, 51, or 52 |
| 1-$X_{1aa}$ (1) | 4 | $X_{1aa}$ is 22, 23, 24, 25, 26, 27, 28, 29, 30, or 31 |
| 1-$X_{1ab}$ (1) | 6 | $X_{1ab}$ is 22, 23, 24, 25, 26, 27, 28, 29, 30, or 31 |
| 1-$X_{1ac}$ (1) | 8 | $X_{1ac}$ is 22, 23, 24, 25, 26, 27, 28, 29, 30, or 31 |
| 1-$X_{1ae}$ (1) | 10 | $X_{1ae}$ is 22, 23, 24, 25, 26, 27, 28, 29, 30, or 31 |
| $X_{1b}$-$X_{2b}$ (2) | 2 | $X_{1b}$ is 43, 44, 45, 46, 47, 48, 49, 50, 51, or 52$X_{2b}$ is 61, 62, 63, 64, 65, 66, 67, 68, 69, or 70 |
| $X_{1aa}$-$X_{2aa}$ (2) | 4 | $X_{1aa}$ is 22, 23, 24, 25, 26, 27, 28, 29, 30, or 31$X_{2aa}$ is 41, 42, 43, 44, 45, 46, 47, 48, 49, 50, or 51 |
| $X_{1ab}$-$X_{2ab}$ (2) | 6 | $X_{1ab}$ is 22, 23, 24, 25, 26, 27, 28, 29, 30, or 31$X_{2ab}$ is 41, 42, 43, 44, 45, 46, 47, 48, 49, 50, or 51 |
| $X_{1ac}$-$X_{2ac}$ (2) | 8 | $X_{1ac}$ is 22, 23, 24, 25, 26, 27, 28, 29, 30, or 31$X_{2ac}$ is 41, 42, 43, 44, 45, 46, 47, 48, 49, 50, or 51 |
| $X_{1ae}$-$X_{2ae}$ (2) | 10 | $X_{1ae}$ is 22, 23, 24, 25, 26, 27, 28, 29, 30, or 31 $X_{2ae}$ is 41, 42, 43, 44, 45, 46, 47, 48, 49, 50, or 51 |
| $X_{2b}$-$X_{3b}$ (3) | 2 | $X_{2b}$ is 61, 62, 63, 64, 65, 66, 67, 68, 69, or 70$X_{3b}$ is 75, 76, 77, 78, 79, 80, 81, 82, 83, 84, 85, 86, 87, or 88 |
| $X_{2aa}$-$X_{3aa}$ (3) | 4 | $X_{2aa}$ is 41, 42, 43, 44, 45, 46, 47, 48, 49, 50, or 51$X_{3aa}$ is 55, 51, 52, 53, 54, 55, 56, 57, 58, 59, 60, 61, 62, 63, 64, 65, 66, 67, 68, 69, 70, 71, 72, 73, or 74 |
| $X_{2ab}$-$X_{3ab}$ (3) | 6 | $X_{2ab}$ is 41, 42, 43, 44, 45, 46, 47, 48, 49, 50, or 51$X_{3ab}$ is 55, 51, 52, 53, 54, 55, 56, 57, 58, 59, 60, 61, 62, 63, 64, 65, 66, 67, 68, 69, 70, 71, 72, 73, or 74 |
| $X_{2ac}$-$X_{3ac}$ (3) | 8 | $X_{2ac}$ is 41, 42, 43, 44, 45, 46, 47, 48, 49, 50, or 51$X_{3ac}$ is 55, 51, 52, 53, 54, 55, 56, 57, 58, 59, 60, 61, 62, 63, 64, 65, 66, 67, 68, 69, 70, 71, 72, 73, or 74 |
| $X_{2ae}$-$X_{3ae}$ (3) | 10 | $X_{2ae}$ is 41, 42, 43, 44, 45, 46, 47, 48, 49, 50, or 51$X_{3ae}$ is 55, 51, 52, 53, 54, 55, 56, 57, 58, 59, 60, 61, 62, 63, 64, 65, 66, 67, 68, 69, 70, 71, 72, 73, or 74 |

TABLE 1-continued

| Amino acids (Domain #) | Parental SEQ ID NO: | Variable definition |
|---|---|---|
| $X_{3b}$-$X_{4b}$ (4) | 2 | $X_{3b}$ is 75, 76, 77, 78, 79, 80, 81, 82, 83, 84, 85, 86, 87, or 88$X_{4b}$ is 95, 96, 97, 98, 99, 100, 101, 102, or 103 |
| $X_{3aa}$-$X_{4aa}$ (4) | 4 | $X_{3aa}$ is 55, 51, 52, 53, 54, 55, 56, 57, 58, 59, 60, 61, 62, 63, 64, 65, 66, 67, 68, 69, 70, 71, 72, 73, or 74$X_{4aa}$ is 79, 80, 81, 82, 83, 84, 85, 86, or 87 |
| $X_{3ab}$-$X_{4ab}$ (4) | 6 | $X_{3ab}$ is 55, 51, 52, 53, 54, 55, 56, 57, 58, 59, 60, 61, 62, 63, 64, 65, 66, 67, 68, 69, 70, 71, 72, 73, or 74$X_{4ab}$ is 78, 79, 80, 81, 82, 83, 84, 85, or 86 |
| $X_{3ac}$-$X_{4ac}$ (4) | 8 | $X_{3ac}$ is 55, 51, 52, 53, 54, 55, 56, 57, 58, 59, 60, 61, 62, 63, 64, 65, 66, 67, 68, 69, 70, 71, 72, 73, or 74$X_{4ac}$ is 79, 80, 81, 82, 83, 84, 85, 86, or 87 |
| $X_{3ae}$-$X_{4ae}$ (4) | 10 | $X_{3ae}$ is 55, 51, 52, 53, 54, 55, 56, 57, 58, 59, 60, 61, 62, 63, 64, 65, 66, 67, 68, 69, 70, 71, 72, 73, or 74$X_{4ae}$ is 77, 78, 79, 80, 81, 82, 83, 84, or 85 |
| $X_{4b}$-$X_{5b}$ (5) | 2 | $X_{4b}$ is 95, 96, 97, 98, 99, 100, 101, 102, or 103$X_{5b}$ is 107, 108, 109, 110, 111, 112, 113, 114, or 115 |
| $X_{4aa}$-$X_{5aa}$ (5) | 4 | $X_{4aa}$ is 79, 80, 81, 82, 83, 84, 85, 86, or 87$X_{5aa}$ is 91, 92, 93, 94, 95, 96, 97, 98, 99, or 100 |
| $X_{4ab}$-$X_{5ab}$ (5) | 6 | $X_{4ab}$ is 78, 79, 80, 81, 82, 83, 84, 85, or 86$X_{5ab}$ is 90, 91, 92, 93, 94, 95, 96, 97, 98, or 99 |
| $X_{4ac}$-$X_{5ac}$ (5) | 8 | $X_{4ac}$ is 79, 80, 81, 82, 83, 84, 85, 86, or 87$X_{5ac}$ is 91, 92, 93, 94, 95, 96, 97, 98, 99, or 100 |
| $X_{4ae}$-$X_{5ae}$ (5) | 10 | $X_{4ae}$ is 77, 78, 79, 80, 81, 82, 83, 84, or 85$X_{5ae}$ is 89, 90, 91, 92, 93, 94, 95, 96, 97, or 98 |
| $X_{5b}$-$X_{6b}$ (6) | 2 | $X_{5b}$ is 107, 108, 109, 110, 111, 112, 113, 114, or 115$X_{6b}$ is 130, 131, or 132 |
| $X_{5aa}$-$X_{6aa}$ (6) | 4 | $X_{5aa}$ is 91, 92, 93, 94, 95, 96, 97, 98, 99, or 100$X_{6aa}$ is 114, 115, or 116 |

In some embodiments, domain 3 may be derived from the same parent as either domain 2, domain 4 or both domain 2 and 4.

As summarized in FIG. 2, in some embodiments, J1 (Junction 1) between domain 1 and domain 2 comprises the consensus sequence $Z_1Z_2W$, wherein $Z_1$ is selected from the group L, V, F, and M, and $Z_2$ is G or K, wherein 2 of the 3 amino acids are found at the C-terminus of the first domain or the N-terminus of the second domain. In some embodiment, J2 (Junction 2) between domain 2 and domain 3 comprises the consensus sequence $CZ_1G$, wherein $Z_1$, is selected from the group H, S, A, L, I, E, K, Q and D, wherein 2 of the 3 amino acids are found at the C-terminus of the second domain or the N-terminus of the third domain. In some embodiment, J3 (Junction 3) between domain 3 and domain 4 comprises the consensus sequence $Z_1Z_2Z_3$, wherein $Z_1$ is selected from the group T, S, P, G and I, $Z_2$ is selected from the group consisting of N, K, V, M, H and Y, and $Z_3$ is selected from the group consisting of H, Y, S, T and P, wherein 2 of the 3 amino acids are found at the C-terminus of the third domain or the N-terminus of the fourth domain. In some embodiment, J4 (Junction 4) between domain 4 and domain 5 comprises the consensus sequence $Z_1CZ_2$, wherein $Z_1$ is selected from the group C, S and V, and $Z_2$ is selected from the group consisting of V, A, I and T, wherein 2 of the 3 amino acids are found at the C-terminus of the fourth domain or the N-terminus of the Fifth domain. In some embodiment, J5 (Junction 1) between the domain 5 and domain 6 comprises the consensus sequence $Z_1Z_2Z_3$, wherein $Z_1$ is selected from the group L, R and V, $Z_2$ is selected from the group consisting of T, Q, Y, F and M, and $Z_3$ is selected from the group consisting of L, F, Y, K, I, Q, V and T, wherein 2 of the 3 amino acids are found at the C-terminus of the fifth domain or the N-terminus of the sixth domain.

An embodiment of the invention provides the following domains (Table 2) for each of the TGF-beta family members that may be recombined to form a chimera of an embodiment having increased or improved biological activity (e.g., resistance to inactivation and the like).

TABLE 2

| | Domain 1 | Domain 2 | Domain 3 | Domain 4 | Domain 5 | Domain 6 |
|---|---|---|---|---|---|---|
| BMP-6 (SEQ ID NO: 2) | 1-47 | 48-65 | 66-85 | 86-99 | 100-111 | 112-132 |
| activin-βA (SEQ ID NO: 4) | 1-27 | 28-45 | 46-68 | 69-83 | 84-95 | 96-116 |
| activin-βB (SEQ ID NO: 6) | 1-27 | 28-45 | 46-68 | 69-82 | 83-94 | 95-115 |
| activin-βC (SEQ ID NO: 8) | 1-27 | 28-45 | 46-68 | 69-83 | 84-95 | 96-116 |
| activin-βE (SEQ ID NO: 10) | 1-27 | 28-45 | 46-68 | 69-81 | 82-93 | 94-114 |

Thus, as illustrated by various embodiments herein, an embodiment provides a chimeric TGF-beta family polypeptide, wherein a first TGF-beta family protein (i.e., a first parental protein), which is BMP-6 (SEQ ID NO:2), is recombined with a second different TGF-beta family protein (i.e., a second parental protein), which is activin, to provide a chimeric polypeptide. (SEQ ID NO:1 shows DNA sequence of BMP-6 DNA.)

In some embodiments, a chimeric polypeptide comprises one or more domains of a BMP-6 protein, wherein the domains of BMP-6 are as described in Table 1, such that a contiguous polypeptide comprising domains 1b2b3b4b5b6b comprises a wild-type BMP-6 following a Methionine residue resulting from the translation initiation codon (ATG). Homologs and proteins having at least about 80%, 81%, 82%, 83%, 84%, 85%, 86%, 87%, 88%, 89%, 90%, 91%, 92%, 93%, 94%, 95%, 96%, 97%, 98%, and 99% identity to the foregoing sequences are also included by the present invention.

In some embodiments, a chimeric polypeptide comprises one or more domains of activin proteins, wherein the domains of activin-βA (SEQ ID NO:4), activin-βB (SEQ ID NO:6), activin-βC (SEQ ID NO:8), and activin-βE (SEQ ID NO:10) are as described in Table 1, such that a contiguous polypeptide comprising domains 1a2a3a4a5a6a comprises a wild-type mature activin-βA, activin-βB, activin-βC, or activin-βE protein or a chimera of activin-βA, activin-βB, activin-βC, and activin-βE. Homologs and proteins having at least about 80%, 81%, 82%, 83%, 84%, 85%, 86%, 87%, 88%, 89%, 90%, 91%, 92%, 93%, 94%, 95%, 96%, 97%, 98%, and 99% identity to the foregoing sequences are also included by the present invention. (SEQ ID NO:3, SEQ ID NO:5, SEQ ID NO:7, and SEQ ID NO:9 show DNA sequences of activin-βA, activin-βB, activin-βC, and activin-βE, respectively.)

In other embodiment, the chimeric polypeptide may be fused to an additional heterologous polypeptide to generate a chimeric fusion polypeptide. The heterologous polypeptide may be, for example, a peptide useful for purification or that permits oligomerization of multiple chimeric polypeptides of an embodiment of the present invention. The heterologous may be chemically conjugated to the chimeric polypeptide or may be operably linked in-frame with a coding sequence for the chimeric polypeptide.

In one embodiment, the amino acid sequence of the chimeric polypeptide is described by an algorithm 1n2n3n4n5n6n, wherein said 1n, 2n, 3n, 4n, 5n, and 6n represent respectively the first, second, third, fourth, fifth, and sixth domain; and said n is either a or b, and wherein said a represents an amino acid sequence derived from the sequence of SEQ ID NO:2; and said b represents an amino acid sequence derived from any one selected from the group consisting of SEQ ID NO:4, SEQ ID NO:6, SEQ ID NO:8, and SEQ ID NO: 10. For example, the chimeric polypeptide may comprise a sequence described by an algorithm selected from the group consisting of 1a2b3b4b5b6b; 1a2b3b4b5b6a; 1a2b3b4b5a6a; 1a2b3b4b5a6b; 1a2b3b4a5a6a; 1a2b3b4a5b6b; 1a2b3b4a5a6b; 1a2b3b4a5b6a; 1a2b3a4a5a6a; 1a2b3a4a5a6b; 1a2b3a4a5b6b; 1a2b3a4a5b6a; 1a2b3a4b5b6b; 1a2b3a4b5b6a; 1a2b3a4b5a6a; 1a2b3a4b5a6b; 1a2a3a4a5a6a; 1a2a3a4a5a6b; 1a2a3a4a5b6a; 1a2a3a4a5b6b; 1a2a3a4b5a6a; 1a2a3a4b5a6b; 1a2a3a4b5b6b; 1a2a3a4b5b6a; 1a2a3a4b5a6b; 1a2a3b4b5b6b; 1a2a3b4b5b6a; 1a2a3b4b5a6a; 1a2a3b4b5a6b; 1a2a3b4a5a6a; 1a2a3b4a5b6b; 1a2a3b4a5a6b; 1a2a3b4a5b6a; 1a2a3b4a5b6b; 1a2a3b4a5a6b; 1b2b3b4b5b6b; 1b2b3b4b5b6a; 1b2b3b4b5a6a; 1b2b3b4b5a6b; 1b2b3b4a5a6a; 1b2b3b4a5b6b; 1b2b3b4a5a6b; 1b2b3b4a5b6a; 1b2b3a4a5a6a; 1b2b3a4a5a6b; 1b2b3a4a5b6b; 1b2b3a4a5b6a; 1b2b3a4b5b6b; 1b2b3a4b5b6a; 1b2b3a4b5a6a; 1b2b3a4b5a6b; 1b2a3a4a5a6a; 1b2a3a4a5a6b; 1b2a3a4a5b6a; 1b2a3a4a5b6b; 1b2a3a4b5a6a; 1b2a3a4b5a6b; 1b2a3a4b5b6b; 1b2a3a4b5b6a; 1b2a3b4b5b6b; 1b2a3b4b5b6a; 1b2a3b4b5a6a; 1b2a3b4b5a6b; 1b2a3b4a5a6b; 1b2a3b4a5a6b; 1b2a3b4a5b6a; 1b2a3b4a5b6b; 1b2a3b4a5a6b, wherein said 1b, 2b, 3b, 4b, 5b, and 6b are respectively said first, second, third, fourth, fifth, and sixth segment of SEQ ID NO:2 and said 1a, 2a, 3a, 4a, 5a, and 6a are respectively said first, second, third, fourth, fifth, and sixth segment of any one selected from the group consisting of SEQ ID NO:4, SEQ ID NO:6, SEQ ID NO:8, and SEQ ID NO: 10.

In one embodiment, the amino acid sequence of the chimeric polypeptide is described by an algorithm 1b2a3b4b5a6a.

In one embodiment, said first domain comprises amino acid residues 1 to 47 of SEQ ID NO:2; said second domain comprises amino acid residues 28 to 45 of SEQ ID NO:4; said third domain comprises amino acid residues 66 to 85 of SEQ ID NO:2; said fourth domain comprises amino acid residues 86 to 99 of SEQ ID NO:2; said fifth domain comprises amino acid residues 84 to 95 of SEQ ID NO:4; and said sixth domain comprises amino acid residues 96 to 116 of SEQ ID NO:4.

In one embodiment, the amino acid sequence of the chimeric polypeptide comprises the sequence as set forth in SEQ ID NO: 12.

In one embodiment, the chimeric polypeptide has at least 95% sequence identity to the sequence as set forth in SEQ ID NO: 12.

In one embodiment, the chimeric polypeptide has at least 97% sequence identity to the amino acid sequence comprising said first domain, said second domain, said third domain, said fourth domain, said fifth domain, and said sixth domain.

In one embodiment, the chimeric polypeptide can form a homo-dimer.

In one embodiment, the chimeric polypeptide can form a hetero-dimer.

In some embodiments, one or more of the domains of a chimeric polypeptide is 100% identical to the parental strand from which each domain was derived. In other embodiments one or more of the domains can comprise an amino acid sequence that has at least 60%, 70%, 80%, 90%, 91%, 92%, 93%, 94%, 95%, 96%, 97%, 98%, or 99% or more identity to a corresponding domain in a parental strand. For example, one of more of the domains may have one or more conservative amino acid substitutions (e.g., 1-5 conservative amino acid substitutions).

In some embodiments, the chimeric TGF-beta family polypeptide may have improved activity compared to one or more of the parental strands from which the chimeric polypeptide is generated. Biological activity of a chimeric polypeptide of an embodiment can be measured using any number of recognized assays in the art for TGF-beta activity. Such assays include, but are not limited to, BIAcore (Surface Plasmon Resonance); $C_2Cl_2$ luciferase assay: Smad 1/5 reporter system; HEK293 luciferase assay: Smad 2/3 reporter system; FSH (Follicle Stimulating Hormone) release assay: in rat pituitary cells; BRE (BMP Response Element) luciferase assay: Smad 1/5 reporter HEK 293 cells; Cripto binding assay: Luciferase response measured in presence/absence of Crptio; Human Stem Cell assay: Maintenance or Differentiation of H9 cells; NMR binding Studies; Micro mass culture: Bone formation measured in Chick embryos; X-ray Crystallography: Determine Structure of ligand:receptor complexes; Native Gel: Visualization of ligand:receptor complexes; Size Exclusion Chromatography (SEC); Visualization of ligand:receptor complexes; Velocity Scan Ultracentrifugation: Visualize ligand:receptor complex formation; and Seldi mass Spectrometry: Accurately determine size of ligands.

The chimeric TGF-beta family polypeptide described herein may be prepared in various forms, such as lysates, crude extracts, or isolated preparations.

In some embodiments, the isolated chimeric polypeptide is a substantially pure polypeptide composition. A "substantially pure polypeptide" refers to a composition in which the polypeptide species is the predominant species present (i.e., on a molar or weight basis it is more, abundant than any other individual macromolecular species in the composition), and is generally a substantially purified composition when the object species comprises at least about 50 percent of the macromolecular species present by mole or % weight. Generally, a substantially pure polypeptide composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

An embodiment contemplates making functional variants by modifying the structure of the chimera. Such modifications may be made, for example, for such purposes as enhancing therapeutic efficacy, or stability (e.g., ex vivo shelf life and resistance to proteolytic degradation in vivo, improve stability, solubility, bioavailability, or biodistribution of the chimeric protein, etc.). For example, but not by way of limitation, the derivatives include a chimera that has been modified, e.g., by acetylation, carboxylation, acylation glycosylation, pegylation, phosphorylation, farnesylation, biotinylation, lipidation, amidation, derivatization by known protecting/blocking groups, proteolytic cleavage, linkage to a cellular ligand or other protein such as an organic deriatizing agent, etc. Any of numerous chemical modifications may be carried out by known techniques, including, but not limited to specific chemical cleavage, acetylation, formylation, metabolic synthesis, etc. Additionally, the derivative may contain one or more non-natural amino acids, such as those with ketone-containing side chain, polyethylene glycols, lipids, poly- or monosaccharide, and phosphates. Effects of such non-natural amino acid elements on the functionality of a chimeric TGF-beta superfamily protein may be tested as described herein for other TGF-beta superfamily protein variants. When a chimeric TGF-beta superfamily protein is produced in cells by cleaving a nascent form of the precursor protein, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct post-translational modification and processing of the precursor protein into a chimeric TGF-beta superfamily protein. In vitro cell-free expression system in combination with its associated engineered tRNA synthase and tRNA can be utilized to ensure the correct modification in a specific amino acid position genetically tagged to introduce non-natural amino acids.

A modified chimera can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

An embodiment contemplates making mutations in a proteolytic cleavage site of the chimera sequence to make the site less susceptible to proteolytic cleavage. Computer analysis (using a commercially available software, e.g., MacVector, Omega, PCGene, Molecular Simulation, Inc.) can be used to identify proteolytic cleavage sites. As will be recognized by one of skill in the art, most of the described mutations, variants or modifications may be made at the nucleic acid level or, in some cases, by post translational modification or chemical synthesis. Such techniques are well known in the art.

An embodiment contemplates specific mutations of a chimera sequences so as to alter the glycosylation of the chimera. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which are specifically recognized by appropriate cellular glycosylation enzymes. The alteration may also be made by the addition of, or substitution by, one or more serine or threonine residues to the sequence of the wild-type polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a chimera may be accomplished chemically and/or enzymatically. Chemical deglycosylation may involve, for example, exposure to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on polypeptides can be achieved by the use of a variety of endo- and exo-glycosidases as described by Thotakura et al. (1987) Meth. Enzymol. 138:350. The nucleic acid and/or amino acid sequence of a propeptide may be adjusted, as appropriate, depending on the type of expression system used, as mammalian, yeast, insect and plant cells may all introduce differing glycosylation patterns that can be affected by the amino acid sequence of the peptide.

In some embodiments, the chimeric polypeptide can be in the form of arrays. The polypeptide may be in a soluble form, for example as solutions in the wells of mircotitre plates, or immobilized onto a substrate. The substrate can be a solid substrate or a porous substrate (e.g, membrane), which can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

An embodiment also provides a polynucleotide encoding the chimeric TGF-beta family polypeptide disclosed herein. The polynucleotide may be operably linked to one or more heterologous regulatory or control sequences that control gene expression to create a recombinant polynucleotide capable of expressing the polypeptide. Expression constructs containing a polynucleotide encoding the chimeric polypeptide can be introduced into appropriate host cells to express the polypeptide. Polynucleotide sequences encoding various domains or full chimera of an embodiment can be determined without undue efforts based upon the various codons that are associated with an amino acid of in a polypeptide. Furthermore, an embodiment provides exemplary sequences of the TGF-β family member. Deriving the sequences of a domain or chimera from the sequences provided herein is readily performed by one of skill in the art. Given the knowledge of specific sequences of the TGF-beta family of proteins, and the specific descriptions of the chimeric polypeptide herein (e.g., the domain structure of the chimeric domains), the nucleic acid sequence of the engineered chimera will be apparent to the skilled artisan. The knowledge of the codons corresponding to various amino acids coupled with the knowledge of the amino acid sequence of the polypeptide allows those skilled in the art to make different polynucleotides encoding the polypeptide of an embodiment. Thus, an embodiment contemplates each and every possible variation of the polynucleotide that could be made by selecting combinations based on possible codon choices, and all such variations are to be considered specifically disclosed for any of the polypeptides described herein.

In some embodiments, the polynucleotide comprises a polynucleotide that encodes the polypeptide described herein but have about 80% or more sequence identity, about 85% or more sequence identity, about 90% or more sequence identity, about 91% or more sequence identity, about 92% or more sequence identity, about 93% or more sequence identity, about 94% or more sequence identity, about 95% or more sequence identity, about 96% or more sequence identity, about 97% or more sequence identity, about 98% or more sequence identity, or about 99% or more sequence identity at the nucleotide level to a reference polynucleotide encoding a chimera or parental TGF-beta family polypeptide.

In some embodiments, the isolated polynucleotide encoding the polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007.

In some embodiments, the polynucleotide is operatively linked to control sequences for the expression of the polynucleotide and/or polypeptide. In some embodiments, the control sequence may be an appropriate promoter sequence, which can be obtained from genes encoding extracellular or intracellular polypeptides, either homologous or heterologous to the host cell.

In some embodiments, the control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used.

In some embodiments, the control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used.

In some embodiments, the control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the domain of the coding region that encodes the secreted polypeptide. Alternatively, the 5' end of the coding sequence may contain a signal peptide coding region that is foreign to the coding sequence. The foreign signal peptide-coding region may be required where the coding sequence does not naturally contain a signal peptide coding region.

An embodiment is further directed to a recombinant expression vector comprising a polynucleotide encoding the chimeric TGF-beta polypeptide described herein, and one or more expression regulating regions such as a promoter and a terminator, a replication origin, etc., depending on the type of hosts into which they are to be introduced. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell or in vitro cell-free reaction mixture into which the vector is to be introduced. The vector may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon, may be used.

In some embodiments, the expression vector contains one or more selectable markers, which permit easy selection of transformed cells. A selectable marker is a gene the product of which provides for biocide or viral resistance, resistance to heavy metals, prototrophy to auxotrophs, and the like.

An embodiment provides a host cell comprising a polynucleotide encoding the chimeric TGF-beta polypeptide, the polynucleotide being operatively linked to one or more control sequences for expression of the fusion polypeptide in the host cell. Host cells for use in expressing the fusion polypeptide encoded by the expression vector of an embodiment are well known in the art. Appropriate culture mediums and growth conditions for the above-described host cells are well known in the art.

An expression vector can be designed for expression of a chimera in prokaryotic or eukaryotic cells. For example, a chimera of an embodiment can be expressed in bacterial or prokaryote cells such as *E. Coli*, insect cells (e.g., the baculovirus expression system), yeast cells, microalgae, plant cells or mammalian cells as well as in vitro cell-free expression system. Some suitable host cells are discussed further in Goeddel, Gene Expression Technology: Methods in Enzymology 185, Academic Press, San Diego, Calif. (1990).

While one example of an expression system discussed is an *E. coli* expression system, to those skilled in the art, these proteins can be easily be cloned into and expressed from a large number of other expression systems. The advantages include, but are not limited to, achieving post-translational modifications as would be seen in the organism the protein was derived from (in this case *H. sapiens*), expression of the ligands without the start methionine required for bacterial expression, and easy incorporation of non-natural amino acids or additional chemical modifications. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31.537); *E. coli* strain W3110 (ATCC 27,325) and K5 772 (ATCC 53,635). In addition to prokaryotes, eukaryotic microbes such as filamentous fungi or yeast are suitable cloning or expression hosts for VEGF-E-encoding vectors. Saccharomyces *cerevisiae* is a commonly used lower eukaryotic host microorganism.

Suitable host cells for the expression of a chimera are derived from unicellular and multicellular organisms. Examples of invertebrate cells include insect cells such as *Drosophila* S2 and *Spodoptera* Sf9, as well as plant cells. Plant expression systems have also been used successfully to express modified proteins. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/DHFR (CHO, Urlaub and Chasin, Proc. Natl. Acad. Sci. USA, 77:4216 (1980)); mouse Sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

Alternate protein expression systems include human embryonic kidney (HEK) 293 cells, insect cell line (*S. frugiperda*) utilizing the baculovirus expression system, yeast expression systems not limited to *P. pastoris* and *S. cerevisiae*, and numerous Microalgae strains. Transgenic animals can be used to express correctly modified protein.

In essence, the animals become living 'bioreactors' capable of expressing large amounts of the desired protein in an easily harvested fluid or tissue, such as the milk from a cow. Cell-free in vitro expression systems using either the bacterial or wheat germ cell lysate can be employed. Cell-free expression system will permit inserting a wide range of non-natural amino acids or epitope tags with higher efficiency and greater specificity.

Examples of bacterial vectors include pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSec1 (Baldari et al., EMBO J. 6:229 (1987)), pMFa (Kurjan and Herskowitz, Cell 30:933 (1982)), pJRY88 (Schultz et al., Gene 54:113 (1987)), and pYES2 (Invitrogen Corporation, San Diego, Calif.). Baculovirus vectors available for expression of nucleic acids to produce proteins in cultured insect cells (e.g., Sf9 cells) include the pAc series (Smith et al., Mol. Cell. Biol. 3:2156 (1983)) and the pVL series (Lucklow and Summers Virology 170:31 (1989)).

Examples of mammalian expression vectors include pWLNEO, pSV2CAT, pOG44, pXT1, pSG (Stratagene) pSVK3, PBPV, pMSG, PSVL (Pharmacia), pCDM8 (Seed, Nature 329:840 (1987)) and pMT2PC (Kaufman et al., EMBO J. 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxyvirus, alphavirus, baculovirus, vaccinia virus, herpes virus. Epstein-Barr virus, adenovirus, geminivirus, and caulimovims vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

The chimera of an embodiment can be made by using methods well known in the art. A polynucleotide can be synthesized by recombinant techniques, such as that provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007. Polynucleotides encoding the enzymes, or the primers for amplification can also be prepared by standard solid-phase methods, according to known synthetic methods, for example using phosphoramidite method described by Beaucage et al., (1981) Tet Lett 22:1859-69, or the method described by Matthes et al., (1984) EMBO J. 3:801-05, e.g., as it is typically practiced in automated synthetic methods. In addition, automated peptide synthesizers are commercially available (e.g., Advanced ChemTech Model 396; Milligen/Bioscarch 9600).

An embodiment is directed to a method to accelerate construction of large chimera libraries. Accordingly, an embodiment provides a recombinant strategy termed RASCH (RAndom Segmental CHimera). It uses a template sequence (first strand from one TGF-beta superfamily member) and a few target sequences (second (third, fourth, fifth, sixth) strand from one or more alternate TGF-beta superfamily members), whose domains are to be linked. The template DNA sequence is used to promote efficient coupling of the target sequences and is degraded once domains are linked. Following the gene construction to create the chimeric sequences, the new ligands are chemically refolded into functional dimer. This dimerization process permits additional diversification of the final sequence by mixing and dimerizing two different sequences of both natural and designer origins. Therefore, the RASCH method can be used to diversify the approximate 40 natural protein sequences of TGF-beta superfamily ligands into ten of thousands or more variant sequences, each distinct from any naturally-occurring TGF-beta superfamily ligand sequences.

Engineered polypeptide expressed in a host cell can be recovered from the cells and or the culture medium using any one or more of the well-known techniques for protein purification, including, among others, lysozyme treatment, sonication, filtration, salting-out, ultra-centrifugation, chromatography, and affinity separation (e.g., substrate bound antibodies).

Chromatographic techniques for isolation of the polypeptide include, among others, reversed phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

Assays to determine activity are well known in the art. An embodiment relates to assays to test for biological activity of chimeric proteins, more preferably, to assays to test for clinical activity. Such activity can include enhanced agonistic or antagonistic TGF-beta activity, combined or novel biological activity, and the like.

In certain embodiments, a chimeric protein of an embodiment comprising an agonist of a TGF-beta superfamily protein comprises an antagonist of a different TGF-beta superfamily protein.

Irrespective of which protein expression, harvesting, and, folding methodologies are used, certain of the subject chimeric proteins can bind, preferentially to a pre-selected receptor and can now be identified using standard methodologies, e.g., ligand/receptor binding assays, well known, and thoroughly documented in the art. See, e.g., Legerski gl al. (1992) Bio h_Biophys. Res. Comm. 183: 672679; Frakar et al. (1978) Biochem. Bio12-hys. Res. Comm 80:849-857; Chio et el. (1990) Nature 343: 266-269; Dahlman et al. (1988) Biochem 27: 1813-1817; Strader et el. (1989) J. Biol. Chem. 264: 13572-13578; and DDowd et al. (1988) J. Biol. Chem. 263: 15985-15992.

Typically, in a ligand/receptor binding assay, the native or parent TGF-beta superfamily member of interest having a known, quantifiable affinity for a pre-selected receptor is labeled with a detectable moiety, for example, a radiolabel, a chromogenic label, or a fluorogenic label. Aliquots of purified receptor, receptor binding domain fragments, or cells expressing the receptor of interest on their surface are incubated with the labeled TGF-beta superfamily member in the presence of various concentrations of the unlabeled chimeric protein. The relative binding affinity of a candidate chimeric protein may be measured by quantitating the ability of the chimeric protein to inhibit the binding of the labeled TGF-beta superfamily member with the receptor. In performing the assay, fixed concentrations of the receptor and the TGF-beta superfamily member are incubated in the presence and absence of unlabeled chimeric protein. Sensitivity may be increased by preincubating the receptor with the chimeric protein before adding the labeled template TGF-beta superfamily member. After the labeled competitor has been added, sufficient time is allowed for adequate competitor binding, and then free and bound labeled TGF-beta superfamily members are separated from one another, and one or the other measured. Labels useful in the practice of the screening procedures include radioactive labels, chromogenic labels, spectroscopic labels such as those disclosed in Haughland (1994) "Handbook of Fluorescent and Research Chemicals," 5 ed. by Molecular Probes, Inc., Eugene, Oreg., or conjugated enzymes having high turnover rates, i.e., horseradish peroxidase, alkaline phosphatase, or agalactosidase, used in combination with chemiluminescent or fluorogenic substrates. The biological activity, namely the agonist or antagonist properties of the resulting chimeric protein constructs can subsequently be characterized using conventional in vivo and in vitro assays that have been developed to measure the biological activity of any TGF-beta superfamily member. It is appreciated, however, the type of assay used preferably depends on the TGF-beta superfamily member upon which the chimeric protein is based The presence of multimers among the subject chimeric proteins can be detected visually either by standard SDS-PAGE in the absence of a reducing agent such as DTT or by HPLC (e.g., C18 reverse phase HPLC). Multimeric proteins of an embodiment can have an apparent molecular weight proportionally greater than the monomeric subunit, e.g., in the range about 28-36 kDa for a dimer, as compared to monomeric subunits, which may have an apparent molecular weight of about 14-18 kDa. The multimeric protein can readily be visualized on an electrophoresis gel by comparison to commercially available molecular weight standards. The dimeric protein also elutes from a C18 RP HPLC (45-50% acetonitrile:0.1% TFA) at a time point different from that for its monomeric counterpart.

A second assay evaluates the presence of dimer (e.g., OP-1 dimers) by its ability to bind to hydroxyapatite. Optimally-folded dimer binds a hydroxyapatite column well in pH7, 10 mM phosphate, 6M urea, and 0.142M NaCl (dimer elutes at 0.25 M NaCl) as compared to monomer, which does not bind substantially at those concentrations (monomer elutes at 0.1M NaCl). A third assay evaluates the presence of dimer by the protein's resistant to trypsin or pepsin digestion. The folded dimeric species is substantially resistant to both enzymes, particularly trypsin, which cleaves only a small portion of the N-terminus of the mature protein, leaving a biologically active dimeric species only slightly smaller in size than the untreated dimer (each monomer in amino acids smaller after trypsin cleavage). By contrast, the monomers and misfolded dimers are substantially degraded. In the assay, the protein is subjected to an enzyme digest using standard conditions, e.g., digestion in a standard buffer such as 50 mM Tris buffer, pH 8, containing 4 M urea, 100 mM NaCl, 0.3% Tween-80 and 20 mM methylamine. Digestion is allowed to occur at 37° C. for on the order of 16 hours, and the product visualized by any suitable means, preferably SDS PAGE.

The biological activity of the subject chimeric proteins, for example, the chimeric proteins having one or more domains from BMPs, can be assessed by any of a number of means as described in WO00/20607. For example, the protein's ability to induce endochondral bone formation can be evaluated using the well characterized rat subcutaneous bone assay. In the assay bone formation is measured by histology, as well as by alkaline phosphatase and/or osteoclacin production. In addition, osteogenic proteins having high specific bone forming activity, such as OP-1, BMP-2, BMR4, BMP-5 and BMP-6, also induce alkaline phosphatase activity in an in vitro rat osteoblast or osteosarcoma cell-based assay. Such assays are well described in the art. See, for example, Sabokdar of al. (1994) Bone and Mineral 27:57-67; Knutsen et al. (1993) Biochem Biophys Res. Commun 194:1352-1358; and Maliakal et al. (1994) Growth Factors 1:227-234).

By contrast, osteogenic proteins having low specific bone forming activity, such as CDMP-1 and CDMP-2, for example, do not induce alkaline phosphatase activity in the cell based osteoblast assay. For example, CDMP-1. CDMP-2 and CMDP-3 all are competent to induce bone formation, although with a lower specific activity than BMP-2, BW-4, BV-5, BMP-6 or OP-1. Conversely, BMP-2, BMP-4, BMP-5, BPyIP-6 and OP-1 all can induce articular cartilage formation, albeit with a lower specific activity than CDMP-1, CDMP-2 or CDMP-3. Accordingly, a chimeric protein having one or more domain from CDMP, designed and described herein to be a chimeric protein competent to induce alkaline phosphatase activity in the cell-based assay, is expected to demonstrate a higher specific bone forming activity in the rat animal bioassay.

The chimeric protein's biological activity can also be readily evaluated by the protein's ability to inhibit epithelial cell growth. A useful, well characterized in vitro assay utilizes mink lung cells or melanoma cells. See WO00/20607. Other assays for other members of the TGF-beta superfamily are well described in the literature and can be performed without undue experimentation.

An embodiment provides methods and agents for control and maintain skeletal muscle mass in a host, preferably a human. Therefore, any chimeric protein of an embodiment that is expected to affect muscle-related function of a TGF-beta superfamily protein such as for example GDF-8 can be tested in whole cells or tissues, in vitro or in vivo, to confirm their ability to modulate skeletal muscle mass. GDF-8 (also known as myostatin) is a negative regulator of skeletal muscle growth. GDF-8 knockout mice have approximately twice the skeletal muscle mass of normal mice. The effects of increased muscle mass on bone modeling may be investigated, e.g., by examining bone mineral content (BMC) and bone mineral density (BMD) in the femora of female GDF-8 knockout mice. Dual-energy X-ray absorptiometry (DEXA) densitometry can be used to measure whole-femur BMC and BMD, and PQCT densitometry can be used to calculate BMC and BMD from cross-sections of tissues. Hamrick, Anat Rec. 2003 May; 272A(1):388-91. As is known in the art, a chimeric protein of an embodiment may be introduced into the GDF-8 knockout mice, and similar assays can be used to determine the effect of the chimeric protein on skeletal muscle mass and bone density.

The dystrophic phenotype in the mdx mouse model of Duchenne muscular dystrophy (DMD) may also be employed to test the biological activity of a chimeric protein of an embodiment. It was reported that blockade of endogenous myostatin by using intraperitoneal injections of blocking antibodies for three months resulted in an increase in body weight, muscle mass, muscle size and absolute muscle strength in mdx mouse muscle along with a significant decrease in muscle degeneration and concentrations of serum creatine kinase. Bogdanovich et al., Nature. 2002 Nov. 28; 420(6914):418-21. Similar study may be employed to determine whether a chimeric protein of an embodiment potentiates or inhibits the endogenous GDF-8 activity.

An embodiment provides methods and agents for modulating neurogenesis. For example, GDF-11 is known to inhibit olfactory epithelium neurogenesis in vitro by inducing p27(Kip1) and reversible cell cycle arrest in progenitors. Wu et al. Neuron. 2003 Jan. 23; 37(2): 197-207. The effect of a chimeric protein of an embodiment on neurogenesis can be similarly tested. Further, the effect of a chimeric protein of an embodiment on GDF-11's effect on neurogenesis can also be tested using similar assays as described in Wu et al. Id.

An embodiment provides methods and agents for stimulating bone formation and increasing bone mass. Therefore, any chimeric protein of an embodiment that is expected to affect bone-related function of a TGF-beta superfamily protein such as for example BMP-2, BMP-3, GDF-10, BMP-4, BMP-7, or BMP-8, can be tested in whole cells or tissues, in vitro or in vivo, to confirm their ability to modulate bone or cartilage growth. Various methods known in the art can be utilized for this purpose.

For example, BMP-3 inhibits BMP2-mediated induction of Msx2 and blocks BMP2-mediated differentiation of osteoprogenitor cells into osteoblasts. Thus, the effect of a subject chimer protein, preferably one comprising a domain from a BMP-2 or BMP-3, on bone or cartilage growth can be determined by their effect on the osteogenic activity of BMP-2, for example, by measuring induction of Msx2 or differentiation of osteoprogenitor cells into osteoblasts in cell based assays (see, e.g., Daluiski et al., Nat. Genet. 2001, 27(1):84-8; Hino et al., Front Biosci. 2004, 9:1520-9). Similarly, a subject chimeric protein, preferably one comprising a domain from a BMP-2 or BMP-3, may be tested for its osteogenic or anti-osteogenic activity or its agonistic or antagonistic effect on BMP-2-mediated osteogenesis.

Another example of cell-based assays includes analyzing the osteogenic or anti-osteogenic activity of a subject chimeric and test compounds in mesenchymal progenitor and osteoblastic cells. To illustrate, recombinant adenoviruses expressing a subject chimeric protein were constructed to infect pluripotent mesenchyimal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8): 1544-52).

Further, an embodiment contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. These references are incorporated by reference herein in their entirety for their disclosure of rat model for study on osteoporotic bone fracture. In certain aspects, an embodiment makes use of fracture healing assays that are known in the art. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

It is understood that the screening assay of an embodiment apply to not only the subject chimeric proteins and variants thereof, but also any test compounds including agonists and antagonist of the chimeric proteins or their variants themselves. Further, these screening assays are useful for drug target verification and quality control purposes.

An embodiment relates to the use of the subject chimeric TGF-beta superfamily proteins to identify compounds which can modulate activities of the chimeric proteins. Compounds identified through this screening can be tested in tissues (e.g., bone and/or cartilage) or cells (e.g., muscle cells) to assess their ability to modulate the test tissues or cells (e.g., bone/cartilage growth or muscle cell growth) in vitro. Optionally, these compounds can further be tested in animal models to assess their ability to modulate, e.g., bone/cartilage growth or muscle control and maintenance in vivo.

A variety of assay formats will suffice and, in light of the present invention, those not expressly described herein will nevertheless be comprehended by one of ordinary skill in the art. As described herein, the test compound (agent) of an embodiment may be created by any combinatorial chemical method. Alternatively, the subject compounds may be naturally occurring biomolecules synthesized in vivo or in vitro. Compounds (agents) to be tested for their ability to act as modulators of bone or cartilage growth can be produced, for example, by bacteria, yeast, plants or other organisms (e.g., natural products), produced chemically (e.g., small molecules, including peptidomimetics), or produced recombinantly. Test compound contemplated by an embodiment include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compound of an embodiment can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase, photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a chimeric TGF-beta superfamily protein and its binding protein (e.g., the chimeric protein itself or a TGF-beta receptor protein or fragments thereof).

Merely to illustrate, in an exemplary screening assay of an embodiment, the compound of interest is contacted with an isolated and purified chimeric protein which is ordinarily capable of binding to a TGF-beta receptor protein or fragments thereof, as appropriate for the intention of the assay. To the mixture comprising a subject chimeric protein and a TGF-beta receptor protein is then added a composition containing a test compound. Detection and quantification of the chimeric protein receptor complexes provides a means for determining the compound's efficacy at inhibiting (or potentiating) complex formation between the chimeric TGF-beta superfamily protein and its binding protein, e.g., the TGF-beta receptor or fragments thereof. The efficacy of the compound can be assessed by generating dose response curves from data obtained using various concentrations of the test compound. Moreover, a control assay can also be performed to provide a baseline for comparison. For example, in a control assay, an isolated and purified chimeric TGF-beta superfamily protein is added to a composition (cell-free or cell-based) containing a TGF-beta receptor protein or fragment thereof, and the formation of the chimeric protein-receptor complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system. Alternatively, cells expressing a TGF-beta receptor protein or fragments thereof on their surfaces can be used in certain assays.

Complex formation between a subject chimeric TGF-beta superfamily protein and its binding protein may be detected by a variety of techniques. For instance, modulation of the formation of complexes can be quantitated using, for example, detectably labeled proteins such as radiolabelled (e.g., 32P, 35S, 14C or 3H), fluorescently labeled (e.g., FITC), or enzymatically labeled chimeric protein or its binding protein, by immunoassay, or by chromatographic detection.

An embodiment contemplates the use of fluorescence polarization assays and fluorescence resonance energy transfer (FRET) assays in measuring, either directly or indirectly, the degree of interaction between a chimeric TGF-beta superfamily protein and its binding protein (e.g., a TGF-beta receptor protein or fragments thereof). Further, other modes of detection such as those based on optical waveguides (PCT Publication WO 96/26432 and U.S. Pat. No. 5,677,196), surface plasmon resonance (SPR), surface charge sensors, and surface force sensors are compatible with many embodiments of the present invention.

Moreover, an embodiment contemplates the use of an interaction trap assay, also known as the "two hybrid assay," for identifying agents that disrupt or potentiate interaction between a chimeric TGF-beta superfamily protein and its binding protein (e.g., a TGF-beta receptor protein or fragments thereof). See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696).

A chimera polynucleotide, a polypeptide, an antibody, a cell and other reagent of an embodiment have a wide variety of uses, both in vitro and in vivo. For example, in representative embodiments, these reagents may be used in vitro or in vivo (e.g., in an animal model) (o study the processes of mineralization, bone formation, and bone loss. Further, "knock in" and "knock out" animals can be used as animal models of disease or as screening tools (discussed more below) for compounds that interact with the chimera polynucleotide or polypeptide. It will be apparent to those skilled in the art that any suitable vector can be used to deliver the polynucleotide to a cell or subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Chimeric polypeptide of an embodiment may be formulated for use in various biological systems including in vivo. Any of a variety of art-known methods can be used to administer a chimera either alone or in combination with other active agents. For example, administration can be parenterally by injection or by gradual infusion over time. The agent (s) can be administered by such means as oral, rectal, buccal (e.g., sublingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, intracavity, and inhalation administration, administration to the liver by intraportal delivery, as well as direct organ injection (e.g., into the liver, into the brain for delivery to the central nervous system, into the pancreas). The most suitable route in any given case will depend on the nature and severity of the condition being treated and on the nature of the particular compound which is being used.

An embodiment also provides a pharmaceutical preparation comprising a subject chimeric protein and a pharmaceutically acceptable carrier. A pharmaceutical preparation may be employed to promote growth of a tissue or diminishing or prevent loss of a tissue in a subject, preferably a human. The targeted tissue can be, for example, bone, cartilage, skeletal muscle, cardiac muscle and/or neuronal tissue.

In another aspect, a chimeric TGF-beta polypeptide can be formulated either alone or in combination with other agents for administration (e.g., as a lotion, cream, spray, gel, or ointment). It may be formulated into liposomes to reduce toxicity or increase bioavailability. Other methods for delivery include oral methods that entail encapsulation of the in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a composition comprising a chimeric TGF-beta polypeptide include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and Fixed oils. Intravenous vehicles include fluid and nutrient replenishers, electrolyte replenishers (such as those based on Ringer's dextrose), and the like. Preservatives and other additives such as, other antimicrobial, anti-oxidants, cheating agents, inert gases and the like also can be included.

An embodiment provides various disease and disorders that may be modulated by a TGF-beta protein family member comprising contacting or administering a therapeutically effective amount of a chimeric TGF-beta polypeptide either alone or in combination with other agents to a subject who has, or is at risk of having, such a disorder.

A therapeutically effective amount can be measured as the amount sufficient to decrease a subject's symptoms associated with the diseases or disorder. Typically, the subject is treated with an amount of a therapeutic composition sufficient to reduce a symptom of a disease or disorder by at least 50%, 90% or 100%. Generally, the optimal dosage will depend upon the disorder and factors such as the weight of the subject, the age, the weight, sex, and degree of symptoms. For example, with respect to bone morphogenesis, optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays, histomorphometric determinations, and tetracycline labeling. Nonetheless, suitable dosages can readily be determined by one skilled in the art. Typically, a suitable dosage is 0.01 to 40 mg/kg body weight, e.g.

As mentioned previously, the composition and the method of an embodiment can include the use of additional (e.g., in addition to a chimeric TGF-beta polypeptide) therapeutic agents (e.g., an inhibitor of TNF, an antibiotic, and the like). The chimeric TGF-beta polypeptide, other therapeutic agent(s), and/or antibiotic(s) can be administered, simultaneously, but may also be administered sequentially.

A pharmaceutical composition comprising a chimera according to an embodiment can be in a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical composition according to an embodiment may be administered locally or systemically. A "therapeutically effective dose" is the quantity of an agent according to an embodiment necessary to prevent, to cure, or at least partially arrest a symptoms associated with a disease or disorder or to promote cell growth, proliferation or differentiation. Amounts effective for this use will, of course, depend on the severity of the disease, disorder, or desired effect and will depend on weight and general state of the subject. Typically, dosages used in vitro may provide useful guidance in the amounts useful for in situ administration of the pharmaceutical composition, and animal models may be used to determine effective dosages for treatment of the disease or disorder. Various considerations are described, e.g., in Langer, Science, 249: 1527, (1990): Gilman et al. (eds.) (1990), each of which is herein incorporated by reference. Dosages of pharmaceutically active compounds can be determined by methods known in the art, see, e.g., Remington's Pharmaceutical Sciences (Maack Publishing Co., Easton. Pa.); Remington. The Science & Practice of Pharmacy, (Lippincott Williams & Wilkins; Twenty first Edition). The therapeutically effective dosage of any specific compound will vary somewhat from compound to compound, and patient to patient, and will depend upon the condition of the patient and the route of delivery. As a general proposition, a dosage from about 0.1 to about 100 mg/kg will have therapeutic efficacy, with all weights being calculated based upon the weight of the compound, including the cases where a salt is employed. Toxicity concerns at the higher level can restrict intravenous dosages to a lower level such as up to about 10 to about 20 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 15 mg/kg can be employed for intramuscular injection. Particular dosages are about 1 µmol/kg to 50 µmol/kg, and more particularly to about 22 µmol/kg and to 33 µmol/kg of the compound for intravenous or oral administration, respectively.

In an embodiment, more than one administration (e.g., two, three, four, or more administrations) can be employed over a variety of lime intervals (e.g., hourly, daily, weekly, monthly, etc.) to achieve therapeutic effects.

The composition and chimera of an embodiment find use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of a liver disease or a bone and cartilage disease.

As used herein, "administering a therapeutically effective amount" is intended to include methods of giving or applying a pharmaceutical composition of an embodiment to a subject that allow the composition to perform its intended therapeutic function.

The pharmaceutical composition can be administered in a convenient manner, such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition should be sterile and should be fluid to the extent that easy syringability exists. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be typical to include isotonic agents, for example, sugars, polyalcohols, such as mannitol, sorbitol, or sodium chloride in the composition. Prolonged absorption of the injectable composition can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assailable edible carrier. The pharmaceutical composition and other ingredients can also be enclosed in a hard or soft-shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic/biocompatible in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic composition or the method of treatment is contemplated. Supplementary active compounds can also be incorporated into the composition.

In certain embodiments, the therapeutic method includes administering the composition topically, systemically, or locally as an implant or device. When administered, the therapeutic composition described by an embodiment is generally in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the chimera of an embodiment may also optionally be included in the composition as described above, may alternatively or additionally, be administered simultaneously or sequentially with the chimera in the methods of the described herein. For example, preferably for bone and/or cartilage formation, the composition would include a matrix capable of delivering a BMP chimera or other therapeutic compounds to the site of bone and/or cartilage damage, providing a structure for the developing bone and cartilage and optimally capable of being resorbed into the body. For example, the matrix may provide slow release of the BMP chimera. Such matrices may be formed of materials presently in use for other implanted medical applications.

The choice of matrix material is based on biocompatibility, biodegradability, mechanical properties, cosmetic appearance and interface properties. The particular application of the subject composition will define the appropriate formulation. Potential matrices for the composition may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the aforementioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

It is especially advantageous to formulate a parenteral composition in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the dosage unit forms of an embodiment are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of the composition containing supplementary active ingredients, the dosage is determined by reference to the usual dose and manner of administration of the said ingredients.

One of the challenges to using a chimera as therapeutics is the ability to deliver the proteins effectively. The chimera of an embodiment can be delivered by several different methods. In the blood stream, the half-life of most TGF-β ligands is on the order of minutes. To compensate for the ligands being degraded so quickly, current therapies involving TGF-β ligands use very high doses of the proteins. Alternatively, several means to directly modify the ligands or delivery systems are available to help improve the stability or sustained release properties of the ligands.

(1) Direct modification of the protein includes PEGylation as one common form of modification. In this method, polyethylene glycol (PEG) is covalently attached to the protein in hopes of improving stability by increasing solubility, resistance to proteolysis, and decreased immunogenicity.

(2) Rational modification of residues on the protein surface. By improving any electrostatic instability, without changing overall protein function, the overall stability of molecule can be improved. Using continuum electrostatic models, residues contributing to instability can be located and then analyzed to see if it can be mutated to a more favorable residue.

(3) Fusing the ligand to another protein or portion of a protein is another technique to increase protein stability and solubility. The antibody constant fragment (Fc) is common fusion partner used to improve the stability and solubility.

(4) The use of liposomes can be used as a protein delivery vehicle. Liposomes are composed of any number of different phospholipids, which self-assemble to form spheres. The protein of interest is encapsulated inside the bilayer, protecting it from the outside environment. The phospholipid composition influences the exact properties of the liposome and can be tailored to release the protein under any number of desired conditions. Polymer/liposome composite systems are also available to be used as delivery systems. Ideally, this type of system combines the advantages of each system to improve protein delivery.

(5) Similar to liposomes, polymers can be used as protein drug delivery systems. The polymers are used to make a matrix, commonly what is termed a hydrogel due to the high water content of the material. The advantage of using the gel is it allows for long term, sustained release as well as protecting the protein from proteolysis. As with the liposomes, the polymers used to make the gel influence its properties. There are two general classifications for the materials used to make the hydorgels: natural and unnatural polymers. Common materials used to create hydrogels using natural polymers include collagen, gelatin, fibrin, Hyaluronic acid, alginate, chitosan, and dextran. Synthetic polymers used to make hydrogels include Poly(ethylene oxide), Poly(acrylic acid). Poly(N-isopropylacrylamide), Poly(vinyl alcohol), and Polyphosphazene.

(6) A different kind of hydrogel can be created without the use of polymers, either natural or unnatural. Considered to be a bioactive glass, or Xerogel, this material is created from silica and calcium phosphate layer capable of absorbing the protein of interest. The Xerogel increases the sustained release time of the protein up to weeks. Results from cell viability assay using osteoblast cell line MC3T3 by MTT assay show that the xerogel material is nontoxic up to the highest concentration of 30 mg/ml in the culture media we tested.

The chimeric polypeptide of an embodiment, alone or in combination, can be used to treat a subject suffering from a liver disease (including, but not limited to, nonalcoholic fatty liver disease, liver fibrosis and hepatic inflammation) or a bone and cartilage disease (including, but not limited to, osteoporosis, periodontal diseases, cartilage disorder and cartilage damage such as injury to the articular cartilage, osteoarthritis, costochondritis, herniation, achondroplasia, relapsing polychondritis, benign or non-cancerous tumors, or malignant or cancerous tumors). The chimera of an embodiment can be used to promote bone and/or cartilage formation, inhibiting bone loss/density or demineralization, promoting bone deposition and the like. Alternatively, the chimera of an embodiment can be used to inhibit excessive bone density and growth.

EXAMPLES

Example 1

Description of Domains (Building Blocks) for Generating Designer Ligand

In order to create the chimera, a first step was deciding where to make the borders for each of the domains. The chimera library has been constructed using activin-pA and BMP-6 as two sequence sources. To design the cut-off regions (Junction) for the domains to make the activin/BMP-6 (AB) chimera, a structure-guided approach combined with protein sequence alignment was used. Initially, the 3-dimensional crystal structures of activin-PA (Harrington et al., 2006) and BMP-6 (Allendorph et al., 2007) were inspected structurally. From this analysis, the ligands were loosely divided into 6 distinct domains (see FIG. 4 for domains 1 through 6). The exact domain junctions were ultimately determined following a protein sequence alignment of the two ligands to minimize any sequence changes of either protein sequence as a result of joining the Junction. Further, the domain boundaries were chosen to be located in structural regions away from receptor binding sites.

Detailed descriptions of Junctions: Between domains 1 and 2 (Junction 1): Focusing on the boundary of domain 1 and domain 2, we found a 10-residue region that is highly conserved between BMP-6 and activin-βA. Indeed, 8 of the 10 residues are identical and the other two are very conservative differences. This area is located in the tip region of Finger 1 and depending of the ligand, makes or is predicted to make limited contacts with either receptor type. Based on the ternary crystal structure of BMP2/BMPRIa/ActRII (Allendorph et al., 2006), only Val-26, Gly-27, and Trp-28 (BMP-2 numbering) generate contacts with the type I receptor. Of these three residues, only Val-26 is different between the ligands, but it is a, very conservative change since the corresponding residue in activin-βA and BMP-6 is Ile-23 and Leu-43, respectively. Since the residues in this region are very similar and not involved in receptor binding, it makes for a good boundary point for domains 1 and 2.

Between domains 2 and 3 (Junction 2): Moving to the boundary region between domains 2 and 3, another good area for our boundary cut-off can be found. Here exists a highly conserved region of 6 residues between activin-βA and BMP-6, where 4 of the 6 residues are identical. When the ligands are properly folded, this region is located in the center of the dimer, with both cyteines participating in the cysteine knot. This is advantageous because the residues here are buried from the surface of the ligands and do not participate in any ligand-receptor interactions.

Between domains 4 and 5 (Junction 4): Similar to the domain 2/3 boundary, the domain 4/5 boundary is situated in an excellent location for the cut-off. Here, we find a 6-residue region that is highly conserved between activin-βA and BMP-6 with 4 identical residues out of the 6 residues, and this region is also buried at the center of the ligand dimer. The 2 cysteine residues participate in both the cysteine knot as well as the inter-monomer disulfide bond. Again, this location prevents the residues in this region from participating in receptor binding interactions.

Between domains 5 and 6 (Junction 5): To extend the design of the BMP-6 and activin-βA chimera, other boundary regions have been chosen to facilitate generating RASCH constructs using all members of the TGF-β superfamily. Along with sharing structural architecture, the TGF-β superfamily ligands seem to have certain regions in their protein sequences that are highly conserved. Interestingly, these regions coincide with the boundary regions chosen for making the BMP-2 and activin-βA chimera. For example, in the boundary region of 4 and 5, most ligands share 3 out of the 4 residues that define the boundary domain. This high degree of similarity, coupled with these regions being isolated from the receptor binding sites, indicates RASCH as the universal strategy to create a library of Designer Ligands with new functionalities.

Between domains 3 and 4 ((Junction 3): The boundary between domains 3 and 4 is subject to structural variability between different subfamilies, in which ligand-receptor assembly mechanism can differ substantially. In certain embodiments, domains 3 and 4 may be treated as one segmental piece such that two domains will be derived from the common parental strand to preserve their structural integrity.

The structural similarity among all TGF-beta superfamily ligands forms the rational basis for designing chimeric protein by exchanging (swapping) related domains of the sequences known to carry out certain functionality such as molecular recognition. Protein engineering of Antibody chain, or more specifically of antibody fragment (Fab), will be a prime example where the basic structural scaffold is built on the Core architecture of the light- and heavy chain sequences, for which six variable loops, three from each of the two chains, are responsible for the role of epitope-binding specificity. In the similar vein, the TGF-beta superfamily ligands share their structural framework as a butterfly-like architecture. A portion(s) of the sequence domains functionally equivalent to variable loop regions of Antibody can then be 'implanted' to transfer recognition specificity from one ligand to another. Our design principle distinguishes itself from the aforementioned 'functional transfer by sequence implantation'. The new chimeric library is created on the basis of structural feasibility of each domain as defined by each Junction. The junctions between the various domains of the TGF-beta family members used to generate the chimera of the disclosure provide useful building blocks of the chimera library. By this reasoning. Junctions 1, 2, 4, and 5 are well defined to be broadly applicable to all TGF-beta superfamily members, whereas Junction 3 is not broadly applicable. The application of Junction 3 in the chimera design depends on the target sequences. The approach maximizes the chance of producing such protein products that are foldable, for which functional characterization will then follow.

Example 2

Generation of TGF-β Chimeras

To generate these novel TGF-β ligands, a modified directed evolution approach was utilized. Typically, this technique involves making a large number of random protein sequences, greater than $10^3$, either by mixing the sequences of homologous genes or inserting random mutations and then screening for the desired ligand properties. Using a structure guided approach, several TGF-β ligand crystal structures were analyzed and divided into 6 distinct domains. These domains roughly encompass the following regions of the ligand: domain 1, N-terminus and beta strand 1; domain 2, beta strand 2; domain 3, pre-helix loop; domain 4, alpha helix; domain 5, beta strand 3; and domain 6, beta stand 4 and C-terminus. Using this protocol, 64 different ligand combinations are possible for each set of TGF-β ligands chosen to be recombined. When two or more parental chains are from different subfamilies (e.g. BMP/GDF v.s. TGFbeta), the difference between their signaling mechanisms may not be captured if domains 3 and 4 are separated. To be broadly applicable as the design principle, it is also part of the design to keep two structural domains, domains 3 and 4, can be treated as one domain of either of the parental gene (referred to as domain 3*4).

The strategy was implemented by making an activin/BMP-6 chimera, where Activin-βA was picked as the target ligand as it has high affinity to TGF-β type II receptors. BMP-6 was chosen as it is biologically very interesting. To design the various domains, a sequence alignment of BMP-6 and activin-βA was performed to locate regions of sequence identity between the ligands (FIG. 4). These regions were used as the boundaries for the different domains. By using these parts of the sequence as the overlap regions for the oligonucleotides during PCR, changes will not be introduced into either the BMP-6 or activin-βA sequences. The sequence alignment was then used in conjunction with data from previously solved BMP-6 and activin-βA structures to ultimately determine the 6 domains (FIG. 4 a-c). Due to limitations with regions of identity between the sequences, the domains had to be shifted slightly from ideal. Particularly, the pre-helix loop and the majority of the α-helix were combined into one domain, while the remainder of the α-helix to the beginning of beta strand 3 was placed into a different domain (FIGS. 4 b and c).

The chimeras are labeled according to the domains they contain. For example, 1b2b3b4a5a6b, in which the b's represent that the domain is taken from BMP-6 and the a's represent that the domain is derived from activin-βA.

One of the activin/BMP-6 chimeras, designated as AB604 (SEQ ID NO: 12) is shown in FIG. 5. (SEQ ID NO:11 shows DNA sequence of AB604.)

Example 3

Protein Expression and Purification

The activin/BMP-6 chimeras were expressed using a typical *E. coli* expression system using *E. coli* BL21(DE3), and the chimeras were found in the inclusion body fractions. The expressed inclusion bodies were isolated, purified, and refolded. The refolded ligands were purified by reversed phase chromatography (GraceVydac). The ligands were lyophilized and re-suspended in 1 mM HCl for use in all cell based assays or 10 mM Na acetate, pH 4 for all biophysical assays. Activin-PA was expressed in a stably transfected CHO cell line and purified using techniques known in the art.

One of the activin/BMP-6 chimeras, designated as AB604 is shown in FIG. 5. AB604 proteins in inclusion bodies were seen as single bands on a reduced, SDS-PAGE gel and found at the expected size of about 15 kDa (FIG. 6; lanes labeled "R"), which means that AB604 exists as monomers in the inclusion bodies. AB604 was refolded in 600 mL volumes at a concentration of 50 mg/L, 100 mg/L or 200 mg/L. After refolding single bands were seen on a non-reduced, SDS-PAGE gel and found at the expected size of about 30 kDa (FIG. 6; lanes labeled "NR"), which means that AB604 exists as dimers after successful refolding. The concentration was chosen based on previously successful BMP-2 and AB204 refoldings.

After refolding, activin/BMP-6 chimeras were purified using Agilent HPLC system with Vydac C4 column (10×250 mm). Purified activin/BMP-6 chimeras were confirmed as disulfide-bonded dimers on a reducing or non-reducing SDS-PAGE gel (FIG. 7).

AB604 showed higher yield than AB204 (one of activin/BMP-2 chimeras). Refolding step is the critical step during production that determines the overall yield of activin/BMP chimera proteins. Thus, the yield was calculated as the amount of successfully refolded proteins in 1 L of refolding volume. The yield of AB604 is 50 mg/L, which is 10-fold higher than the yield of AB204 (TABLE 3).

TABLE 3

|  | AB604 | AB204 |
| --- | --- | --- |
| Refolding Volume | 600 mL | 200 L |
| Amount of the recovered protein after refolding | 120 mg | 50 g |
| Purified amount | 30 mg | 1 g |
| Yield(Basis: 1 L refolding volume) | 50 mg/L | 5 mg/L |

Example 4

Smad-1 Signaling Activity

To be considered a successful ligand, the activin/BMP-6 chimeras not only have to be refoldable but they also need to display signaling characteristics. To test for these properties, activin/BMP-6 chimeras, regardless of refolding efficiency, were initially subjected to signaling activity assays. BMP-like signaling characteristics were tested using a whole cell luciferase reporter assay sensitive to Smad-1 signaling activation (as described below). It was previously shown that BMP-2 shows higher Smad-1 signaling activity compared to BMP-6 (FIG. 3). AB604 showed higher activity than BMP-6, and surprisingly even higher activity than BMP-2 as well (FIG. 8).

Furthermore, Smad-1 signaling activity of AB604 was 7-fold stronger than that of AB204 in terms of $EC_{50}$ values (FIG. 9).

Smad-1 Luciferase Assays in C2C12 Cells were performed as the following. Smad1-dependent luciferase assays were performed using techniques known in the art. In brief, C2C12 myoblast cells are cultured in Dulbecco's minimum essential medium (DMEM)+10% FBS supplemented with L-Glutamine and antibiotics. For luciferase reporter assays, cells were trypsinized, washed twice with PBS and plated into 96-well plates with OptiMEM containing 1.0% FBS. Then, cells were transfected with 1147Id1-luciferase construct containing the Smad binding sites (Id1-Luc), a Smad1 expression construct, and a CAGGS-LacZ plasmid by using Fugenc6 (Roche) according to the manufacturer's instruction and cells were stimulated with increasing amounts (0.4 ng/ml, 1.2 ng/ml, 3.7 ng/ml, 11 ng/ml, 33 ng/ml, 100 ng/ml, 333 ng/ml, 1,000 ng/ml, 3, 333 ng/ml, and 10,000 ng/ml) of BMP-6, BMP-2 or activin/BMP-6 chimeras added 24 hours post transfection. Luciferase activity was measured 16 hours after stimulation with ligands and the values were normalized for transfection efficiency by using beta-galactosidase activity.

Example 5

Smad-2 Signaling Activity

Since activin/BMP6 chimeras also contain sequences of activin A, activin-like signaling characteristics of activin/BMP-6 chimeras were tested using a whole cell luciferase reporter assay sensitive to Smad-2 signaling activation (as described below). TGFβ1 was used as a positive control since it is well known that TGFβ1 has Smad-2 signaling activity. AB604 showed almost no signaling activity in Smad-2 signaling pathway, in which TGFβ1, however, exhibited its activity as expected (FIG. 10). In summary, AB604, one of the activin/BMP6 chimeras, consisting of sequences of activin A and BMP6, inherited its signaling property from BMP6, but not from activin A.

Smad-2 Luciferase Assays in HEK293T cells were performed as the following. Smad2-dependent luciferase assays were performed using techniques known in the art. In brief, HEK293T cells are cultured in Dulbecco's minimum essential medium (DMEM)+10% FBS supplemented with L-Glutamine and antibiotics. For luciferase reporter assays, cells were trypsinized, washed twice with PBS and plated into 96-well plates with OptiMEM containing 1.0% FBS. Then, cells were transfected with A3 Lux construct containing three repeats of activing response elements (ARE), a FAST2 expression construct, and a beta-galactosidase expression plasmid using Fugene6 (Roche) according to the manufacturer's instruction and cells were stimulated with increasing amounts of ligands (for example, 0.01 ng/ml, 0.1 ng/ml, 1.0 ng/ml, 10 ng/ml, 100 ng/ml of AB604 or 0.0005 ng/ml, 0.005 ng/ml, 0.05 ng/ml, 0.5 ng/ml, 5 ng/ml, 50 ng/ml, and 500 ng/ml of TGFβ1) added 24 hours post transfection. Luciferase activity was measured 16 hours after stimulation with ligands and the values were normalized for transfection efficiency by using beta-galactosidase activity.

Example 6

Inhibition of TGFβ Signaling

AB604 was shown to inhibit the signaling activities of TGFβ1 more potently than BMP6 in HEK293T cells as observed by a luciferase reporter assay. When TGFβ1-responsive A3 promoter was activated by TGFβ1 in HEK293T cells in the presence or absence of BMP6 or AB604 at various concentrations, the maximally attainable signaling activity by TGFβ1 was suppressed by the presence of BMP6 or AB604 in a dose-dependent manner (FIG. 11 to FIG. 14). This suppressive effect was more prominent by AB604 than by BMP6. For example, FIG. 12 and FIG. 14 show dose-dependent decreases of TGFβ1-mediated luciferase activities by BMP6 and AB604, respectively. AB604 displayed a statistically significant reduction of TGFβi activities already at 1 ng/ml (FIG. 12), whereas BMP6 did so at 100 ng/ml (FIG. 14)

Example 7

Noggin Sensitivity

Figure 15B:
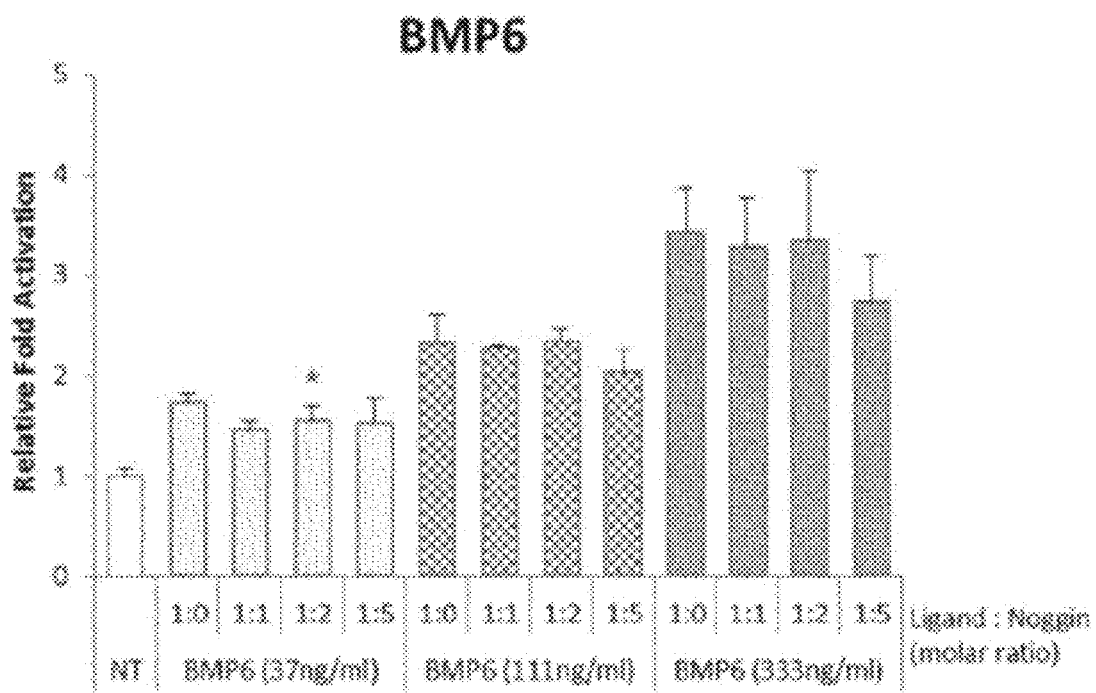
Figure 15C:
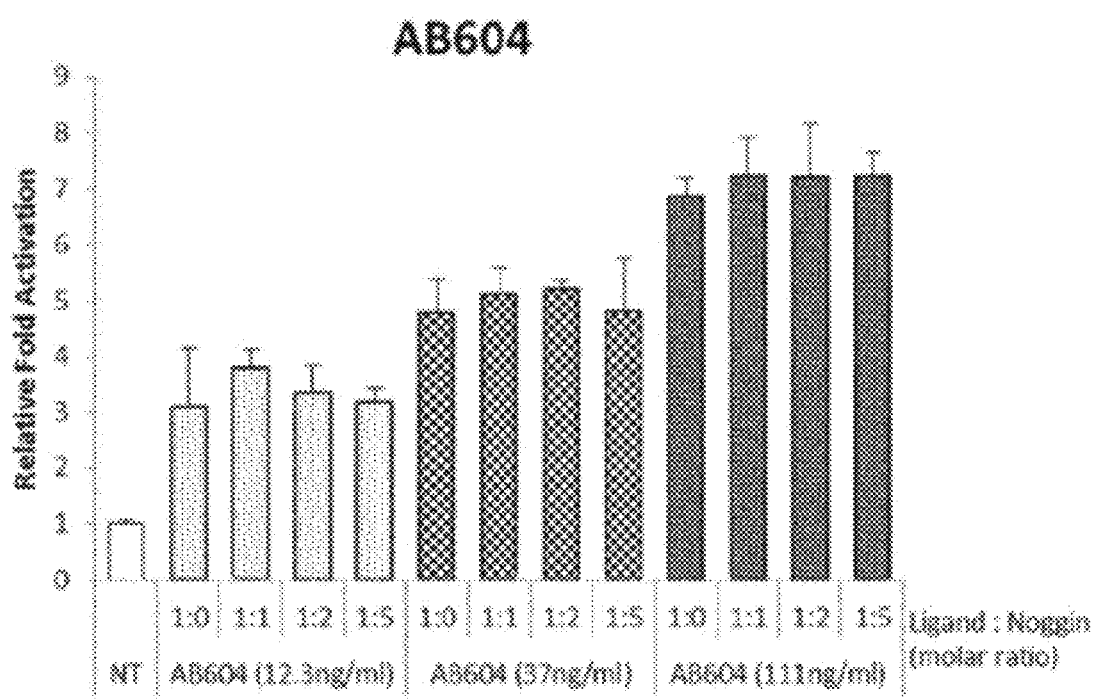

BMP2 signaling is regulated by a natural antagonist noggin, which binds BMP2 and prevents it from binding to its cognate receptors on cell membranes. BMP6 is known to be weakly inhibited by noggin. BMP-responsive luciferase reporter assay in C2C12 cells was used to see whether AB604 is sensitive to noggin or not. C2C12 cells were transiently transfected with Id1-luc, Smad1, and β-galactosidase and then treated with BMP2, BMP6, or AB604 at various concentrations with the indicated molar ratio of noggin supplemented. All of BMP2, BMP6, or AB604 exhibited dose-dependent increases of luciferase activities (FIG. 15), but the suppression of the activity by noggin was only observed in BMP2 (FIG. 15A). The activities of BMP6 or AB604 was not significantly affected by noggin, suggesting noggin-insensitivity of both BMP6 and AB604.

Example 8

Activation of Hepcidin Gene Expression

BMP6 regulates the expression of hepcidin in hepatocytes. Hepcidin is known as a master regulator of systemic and hepatic iron homeostasis, by its action of degrading ferroportin (FPN), an iron-efflux transporter in cell membranes. The effects of BMP6 and AB604 in inducing hepcidin gene expression were tested in Hep3B and HepG2 cells. Both BMP6 and AB604 have increased mRNA level of hepcidin significantly in both Hep3B cells and HepG2 cells, compared to the control. Moreover, the increase of mRNA level of hepcidin was significantly greater in AB604-treated cells than BMP6-treated counterparts (FIG. 16). The dose-dependent profile of hepcidin gene expression demonstrated the higher potency of AB604 compared to that of BMP6, where EC50 values of BMP6 and AB604 exhibited 3-fold differences (12.89 ng/ml for BMR6, 4.42 ng/ml for AB604) (FIG. 17).

Example 9

Phosphorylation of SMAD Proteins

Signaling of TGFβ superfamily ligands involves SMAD proteins in cytoplasm. For example, BMP6 phophorylates SMAD1/5/8 and Activin A or TGFβ1 phophorylate SMAD2/3, SMAD1/5/8 refers to SMAD1, SMAD5, or SMAD8, and SMAD2/3 refers to SMAD2 or SMAD3. Once phosphorylated, these receptor SMADs (R-SMAD) such as SMAD1/5/8 or SMAD2/3 form complex with Co-SMAD or SMAD4, and subsequently go into nucleus to regulate expression of specific target genes. Which SMAD proteins are phosphorylated by AB604 was confirmed by western blot analysis in three different cell lines; C2C12, HEK293T, and HepG2. Cells were treated with TGFβ1, BMP6, or AB604 for 30 minutes or 60 minutes, and then phosphoSMAD1/5/8 or phospho-SMAD2 levels were visualized by western blot. AB604 treatment led to a strong phosphorylation of SMAD1/5/8 in all three cell lines. However, BMP6 showed less prominent phosphorylation of SMAD1/5/8 in C2C12 or HEK293T cells, compared to AB604, and almost did not phosphorylate SMAD1/5/8 in HepG2 cells. TGFβ1 also showed some degree of phosphorylation in C2C12 cells, but not in other cell lines. Taken together, AB604 causes the most significant level of SMAD1/5/8 phosphorylation (FIG. 18). On the other hand, SMAD2 phosphorylation was strong by TGFβ1 in all three cell lines. Interestingly, AB604 was also able to phosphorylate SMAD2 only in HEK293T cells (FIG. 19).

The invention claimed is:

1. A polypeptide capable of binding to one or more of Transforming Growth Factor-beta (TGF-β) superfamily members; or one or more of TGF-β receptors, and comprising the sequence of SEQ ID NO:12.

2. A homo-dimer of the polypeptide of claim 1.

* * * * *

SEQUENCE LISTING

<160> NUMBER OF SEQ ID NOS: 36

<210> SEQ ID NO 1
<211> LENGTH: 396
<212> TYPE: DNA
<213> ORGANISM: Homo sapiens

<400> SEQUENCE: 1

```
caacagagtc gtaatcgctc tacccagtcc caggacgtgg cgcgggtctc cagtgcttca    60
gattacaaca gcagtgaatt gaaaacagcc tgcaggaagc atgagctgta tgtgagtttc   120
caagacctgg gatggcagga ctggatcatt gcacccaagg gctatgctgc caattactgt   180
gatggagaat gctccttccc actcaacgca cacatgaatg caaccaacca cgcgattgtg   240
cagaccttgg ttcaccttat gaaccccgag tatgtcccca aaccgtgctg tgcgccaact   300
aagctaaatg ccatctcggt tctttacttt gatgacaact ccaatgtcat tctgaaaaaa   360
tacaggaata tggttgtaag agcttgtgga tgccac                             396
```

<210> SEQ ID NO 2
<211> LENGTH: 132
<212> TYPE: PRT
<213> ORGANISM: Homo sapiens

<400> SEQUENCE: 2

Gln Gln Ser Arg Asn Arg Ser Thr Gln Ser Gln Asp Val Ala Arg Val
1               5                   10                  15

Ser Ser Ala Ser Asp Tyr Asn Ser Ser Glu Leu Lys Thr Ala Cys Arg
            20                  25                  30

Lys His Glu Leu Tyr Val Ser Phe Gln Asp Leu Gly Trp Gln Asp Trp
        35                  40                  45

Ile Ile Ala Pro Lys Gly Tyr Ala Ala Asn Tyr Cys Asp Gly Glu Cys
    50                  55                  60

Ser Phe Pro Leu Asn Ala His Met Asn Ala Thr Asn His Ala Ile Val
65                  70                  75                  80

Gln Thr Leu Val His Leu Met Asn Pro Glu Tyr Val Pro Lys Pro Cys
                85                  90                  95

Cys Ala Pro Thr Lys Leu Asn Ala Ile Ser Val Leu Tyr Phe Asp Asp
            100                 105                 110

Asn Ser Asn Val Ile Leu Lys Lys Tyr Arg Asn Met Val Val Arg Ala
        115                 120                 125

Cys Gly Cys His
    130

<210> SEQ ID NO 3
<211> LENGTH: 348
<212> TYPE: DNA
<213> ORGANISM: Homo sapiens

<400> SEQUENCE: 3

```
ggcttggagt gtgatggcaa ggtcaacatc tgctgtaaga acagttcttt tgtcagtttc    60
aaggacatcg gctggaatga ctggatcatt gctccctctg ctatcatgc caactactgc   120
gagggtgagt gcccgagcca tatagcaggc acgtccgggt cctcactgtc cttccactca   180
acagtcatca ccactaccg catgcgggc catagcccct tgccaacct caaatcgtgc   240
tgtgtgccca ccaagctgag acccatgtcc atgttgtact atgatgatgg tcaaaacatc   300
atcaaaaagg acattcagaa catgatcgtg gaggagtgtg ggtgctca               348
```

<210> SEQ ID NO 4
<211> LENGTH: 116
<212> TYPE: PRT
<213> ORGANISM: Homo sapiens

<400> SEQUENCE: 4

Gly Leu Glu Cys Asp Gly Lys Val Asn Ile Cys Cys Lys Lys Gln Phe

```
              1               5              10              15
            Phe Val Ser Phe Lys Asp Ile Gly Trp Asn Asp Trp Ile Ile Ala Pro
                            20                  25                  30

Ser Gly Tyr His Ala Asn Tyr Cys Glu Gly Glu Cys Pro Ser His Ile
                            35                  40                  45

Ala Gly Thr Ser Gly Ser Ser Leu Ser Phe His Ser Thr Val Ile Asn
                            50                  55                  60

His Tyr Arg Met Arg Gly His Ser Pro Phe Ala Asn Leu Lys Ser Cys
             65                  70                  75                  80

Cys Val Pro Thr Lys Leu Arg Pro Met Ser Met Leu Tyr Tyr Asp Asp
                            85                  90                  95

Gly Gln Asn Ile Ile Lys Lys Asp Ile Gln Asn Met Ile Val Glu Glu
                           100                 105                 110

Cys Gly Cys Ser
                           115
```

<210> SEQ ID NO 5
<211> LENGTH: 345
<212> TYPE: DNA
<213> ORGANISM: Homo sapiens

<400> SEQUENCE: 5

```
ggcctggagt gcgatggccg gaccaacctc tgttgcaggc aacagttctt cattgacttc        60
cgcctcatcg gctggaacga ctggatcata gcacccaccg gctactacgg caactactgt       120
gagggcagct gcccagccta cctggcaggg gtccccggct ctgcctcctc cttccacacg       180
gctgtggtga accagtaccg catgcggggt ctgaaccccg gcacggtgaa ctcctgctgc       240
attcccacca agctgagcac catgtccatg ctgtacttcg atgatgagta caacatcgtc       300
aagcgggacg tgcccaacat gattgtggag gagtgcggct gcgcc                       345
```

<210> SEQ ID NO 6
<211> LENGTH: 115
<212> TYPE: PRT
<213> ORGANISM: Homo sapiens

<400> SEQUENCE: 6

```
            Gly Leu Glu Cys Asp Gly Arg Thr Asn Leu Cys Cys Arg Gln Gln Phe
             1               5                  10                  15

Phe Ile Asp Phe Arg Leu Ile Gly Trp Asn Asp Trp Ile Ile Ala Pro
                            20                  25                  30

Thr Gly Tyr Tyr Gly Asn Tyr Cys Glu Gly Ser Cys Pro Ala Tyr Leu
                            35                  40                  45

Ala Gly Val Pro Gly Ser Ala Ser Ser Phe His Thr Ala Val Val Asn
                            50                  55                  60

Gln Tyr Arg Met Arg Gly Leu Asn Pro Gly Thr Val Asn Ser Cys Cys
             65                  70                  75                  80

Ile Pro Thr Lys Leu Ser Thr Met Ser Met Leu Tyr Phe Asp Asp Glu
                            85                  90                  95

Tyr Asn Ile Val Lys Arg Asp Val Pro Asn Met Ile Val Glu Glu Cys
                           100                 105                 110

Gly Cys Ala
                           115
```

<210> SEQ ID NO 7
<211> LENGTH: 348
<212> TYPE: DNA

<213> ORGANISM: Homo sapiens

<400> SEQUENCE: 7

```
ggcatcgact gccaaggagg gtccaggatg tgctgtcgac aagagttttt tgtggacttc      60
cgtgagattg ctggcacga ctggatcatc cagcctgagg gctacgccat gaacttctgc     120
atagggcagt gcccactaca catagcaggc atgcctggta ttgctgcctc ctttcacact     180
gcagtgctca atcttctcaa ggccaacaca gctgcaggca ccactggagg gggctcatgc     240
tgtgtaccca cggcccggcg ccccctgtct ctgctctatt atgacaggga cagcaacatt     300
gtcaagactg acatacctga catggtagta gaggcctgtg ggtgcagt                   348
```

<210> SEQ ID NO 8
<211> LENGTH: 116
<212> TYPE: PRT
<213> ORGANISM: Homo sapiens

<400> SEQUENCE: 8

```
Gly Ile Asp Cys Gln Gly Gly Ser Arg Met Cys Cys Arg Gln Glu Phe
1               5                   10                  15
Phe Val Asp Phe Arg Glu Ile Gly Trp His Asp Trp Ile Ile Gln Pro
            20                  25                  30
Glu Gly Tyr Ala Met Asn Phe Cys Ile Gly Gln Cys Pro Leu His Ile
        35                  40                  45
Ala Gly Met Pro Gly Ile Ala Ala Ser Phe His Thr Ala Val Leu Asn
    50                  55                  60
Leu Leu Lys Ala Asn Thr Ala Ala Gly Thr Thr Gly Gly Gly Ser Cys
65                  70                  75                  80
Cys Val Pro Thr Ala Arg Arg Pro Leu Ser Leu Leu Tyr Tyr Asp Arg
                85                  90                  95
Asp Ser Asn Ile Val Lys Thr Asp Ile Pro Asp Met Val Val Glu Ala
            100                 105                 110
Cys Gly Cys Ser
        115
```

<210> SEQ ID NO 9
<211> LENGTH: 342
<212> TYPE: DNA
<213> ORGANISM: Homo sapiens

<400> SEQUENCE: 9

```
acccccacct gtgagcctgc gacccccctta tgttgcaggc gagaccatta cgtagacttc      60
caggaactgg gatggcggga ctggatactg cagcccgagg ggtaccagct gaattactgc     120
agtgggcagt gccctcccca cctggctggc agcccaggca ttgctgcctc tttccattct     180
gccgtcttca gcctcctcaa agccaacaat ccttggcctg ccagtacctc ctgttgtgtc     240
cctactgccc gaaggcccct ctctctcctc tacctggatc ataatggcaa tgtggtcaag     300
acggatgtgc cagatatggt ggtggaggcc tgtggctgca gc                         342
```

<210> SEQ ID NO 10
<211> LENGTH: 114
<212> TYPE: PRT
<213> ORGANISM: Homo sapiens

<400> SEQUENCE: 10

```
Thr Pro Thr Cys Glu Pro Ala Thr Pro Leu Cys Arg Arg Asp His
1               5                   10                  15
```

```
Tyr Val Asp Phe Gln Glu Leu Gly Trp Arg Asp Trp Ile Leu Gln Pro
            20                  25                  30

Glu Gly Tyr Gln Leu Asn Tyr Cys Ser Gly Gln Cys Pro Pro His Leu
        35                  40                  45

Ala Gly Ser Pro Gly Ile Ala Ala Ser Phe His Ser Ala Val Phe Ser
    50                  55                  60

Leu Leu Lys Ala Asn Asn Pro Trp Pro Ala Ser Thr Ser Cys Cys Val
65                  70                  75                  80

Pro Thr Ala Arg Arg Pro Leu Ser Leu Leu Tyr Leu Asp His Asn Gly
                85                  90                  95

Asn Val Val Lys Thr Asp Val Pro Asp Met Val Val Glu Ala Cys Gly
            100                 105                 110

Cys Ser

<210> SEQ ID NO 11
<211> LENGTH: 396
<212> TYPE: DNA
<213> ORGANISM: Artificial Sequence
<220> FEATURE:
<223> OTHER INFORMATION: AB604 DNA

<400> SEQUENCE: 11
caacagagtc gtaatcgctc tacccagtcc caggacgtgg cgcgggtctc cagtgcttca      60
gattacaaca gcagtgaatt gaaaacagcc tgcaggaagc atgagctgta tgtgagtttc     120
caagacctgg gatggcagga ctggattatc gcgccgagtg gctatcacgc caactactgc     180
gagggtgaat gtccgttccc actcaacgca cacatgaatg caaccaacca cgcgattgtg     240
cagaccttgg ttcaccttat gaaccccgag tatgtcccca accgtgctg tgcgccaacc      300 aaactgcgtc cgatgtccat gctgtattac gatgacggcc agaacatcat caaaaaagat     360
atccaaaaca tgatcgtcga agaatgcggt tgtagc                                396

<210> SEQ ID NO 12
<211> LENGTH: 132
<212> TYPE: PRT
<213> ORGANISM: Artificial Sequence
<220> FEATURE:
<223> OTHER INFORMATION: AB604 Polypeptide

<400> SEQUENCE: 12

Gln Gln Ser Arg Asn Arg Ser Thr Gln Ser Gln Asp Val Ala Arg Val
1               5                   10                  15

Ser Ser Ala Ser Asp Tyr Asn Ser Ser Glu Leu Lys Thr Ala Cys Arg
            20                  25                  30

Lys His Glu Leu Tyr Val Ser Phe Gln Asp Leu Gly Trp Gln Asp Trp
        35                  40                  45

Ile Ile Ala Pro Ser Gly Tyr His Ala Asn Tyr Cys Glu Gly Glu Cys
    50                  55                  60

Pro Phe Pro Leu Asn Ala His Met Asn Ala Thr Asn His Ala Ile Val
65                  70                  75                  80

Gln Thr Leu Val His Leu Met Asn Pro Glu Tyr Val Pro Lys Pro Cys
                85                  90                  95

Cys Ala Pro Thr Lys Leu Arg Pro Met Ser Met Leu Tyr Tyr Asp Asp
            100                 105                 110

Gly Gln Asn Ile Ile Lys Lys Asp Ile Gln Asn Met Ile Val Glu Glu
        115                 120                 125

Cys Gly Cys Ser
```

-continued

130

<210> SEQ ID NO 13
<211> LENGTH: 114
<212> TYPE: PRT
<213> ORGANISM: Homo sapiens

<400> SEQUENCE: 13

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 14
<211> LENGTH: 110
<212> TYPE: PRT
<213> ORGANISM: Homo sapiens

<400> SEQUENCE: 14

Gln Trp Ile Glu Pro Arg Asn Cys Ala Arg Arg Tyr Leu Lys Val Asp
1               5                   10                  15

Phe Ala Asp Ile Gly Trp Ser Glu Trp Ile Ile Ser Pro Lys Ser Phe
            20                  25                  30

Asp Ala Tyr Tyr Cys Ser Gly Ala Cys Gln Phe Pro Met Pro Lys Ser
        35                  40                  45

Leu Lys Pro Ser Asn His Ala Thr Ile Gln Ser Ile Val Arg Ala Val
    50                  55                  60

Gly Val Val Pro Gly Ile Pro Glu Pro Cys Cys Val Pro Glu Lys Met
65                  70                  75                  80

Ser Ser Leu Ser Ile Leu Phe Phe Asp Glu Asn Lys Asn Val Val Leu
                85                  90                  95

Lys Val Tyr Pro Asn Met Thr Val Glu Ser Cys Ala Cys Arg
            100                 105                 110

<210> SEQ ID NO 15
<211> LENGTH: 116
<212> TYPE: PRT
<213> ORGANISM: Homo sapiens

<400> SEQUENCE: 15

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115

<210> SEQ ID NO 16
<211> LENGTH: 132
<212> TYPE: PRT
<213> ORGANISM: Homo sapiens

<400> SEQUENCE: 16

Asn Gln Asn Arg Asn Lys Ser Ser His Gln Asp Ser Ser Arg Met
1               5                   10                  15

Ser Ser Val Gly Asp Tyr Asn Thr Ser Glu Gln Lys Gln Ala Cys Lys
            20                  25                  30

Lys His Glu Leu Tyr Val Ser Phe Arg Asp Leu Gly Trp Gln Asp Trp
        35                  40                  45

Ile Ile Ala Pro Glu Gly Tyr Ala Ala Phe Tyr Cys Asp Gly Glu Cys
    50                  55                  60

Ser Phe Pro Leu Asn Ala His Met Asn Ala Thr Asn His Ala Ile Val
65                  70                  75                  80

Gln Thr Leu Val His Leu Met Phe Pro Asp His Val Pro Lys Pro Cys
                85                  90                  95

Cys Ala Pro Thr Lys Leu Asn Ala Ile Ser Val Leu Tyr Phe Asp Asp
            100                 105                 110

Ser Ser Asn Val Ile Leu Lys Lys Tyr Arg Asn Met Val Val Arg Ser
        115                 120                 125

Cys Gly Cys His
        130

<210> SEQ ID NO 17
<211> LENGTH: 139
<212> TYPE: PRT
<213> ORGANISM: Homo sapiens

<400> SEQUENCE: 17

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

```
Ser Val Leu Tyr Phe Asp Asp Ser Asn Val Ile Leu Lys Lys Tyr
            115                 120                 125

Arg Asn Met Val Val Arg Ala Cys Gly Cys His
130                 135
```

<210> SEQ ID NO 18
<211> LENGTH: 139
<212> TYPE: PRT
<213> ORGANISM: Homo sapiens

<400> SEQUENCE: 18

```
Ala Val Arg Pro Leu Arg Arg Gln Pro Lys Lys Ser Asn Glu Leu
1               5                   10                  15

Pro Gln Ala Asn Arg Leu Pro Gly Ile Phe Asp Asp Val His Gly Ser
                20                  25                  30

His Gly Arg Gln Val Cys Arg Arg His Glu Leu Tyr Val Ser Phe Gln
            35                  40                  45

Asp Leu Gly Trp Leu Asp Trp Val Ile Ala Pro Gln Gly Tyr Ser Ala
50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Met Pro
                85                  90                  95

Asp Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
            115                 120                 125

Arg Asn Met Val Val Lys Ala Cys Gly Cys His
130                 135
```

<210> SEQ ID NO 19
<211> LENGTH: 110
<212> TYPE: PRT
<213> ORGANISM: Homo sapiens

<400> SEQUENCE: 19

```
Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
                20                  25                  30

Glu Ala Tyr Glu Cys Lys Gly Gly Cys Phe Phe Pro Leu Ala Asp Asp
            35                  40                  45

Val Thr Pro Thr Lys His Ala Ile Val Gln Thr Leu Val His Leu Lys
50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110
```

<210> SEQ ID NO 20
<211> LENGTH: 108
<212> TYPE: PRT
<213> ORGANISM: Homo sapiens

<400> SEQUENCE: 20

```
Asn Ala Lys Gly Asn Tyr Cys Lys Arg Thr Pro Leu Tyr Ile Asp Phe
```

```
                1               5                   10                  15
        Lys Glu Ile Gly Trp Asp Ser Trp Ile Ile Ala Pro Pro Gly Tyr Glu
                        20                  25                  30

Ala Tyr Glu Cys Arg Gly Val Cys Asn Tyr Pro Leu Ala Glu His Leu
                        35                  40                  45

Thr Pro Thr Lys His Ala Ile Ile Gln Ala Leu Val His Leu Lys Asn
                        50                  55                  60

Ser Gln Lys Ala Ser Lys Ala Cys Cys Val Pro Thr Lys Leu Glu Pro
        65                      70                  75                  80

Ile Ser Ile Leu Tyr Leu Asp Lys Gly Val Val Thr Tyr Lys Phe Lys
                                85                  90                  95

Tyr Glu Gly Met Ala Val Ser Glu Cys Gly Cys Arg
                        100                 105

<210> SEQ ID NO 21
<211> LENGTH: 125
<212> TYPE: PRT
<213> ORGANISM: Homo sapiens

<400> SEQUENCE: 21

Gln Ala Asp Gly Ile Ser Ala Glu Val Thr Ala Ser Ser Lys His
        1               5                   10                  15

Ser Gly Pro Glu Asn Asn Gln Cys Ser Leu His Pro Phe Gln Ile Ser
                        20                  25                  30

Phe Arg Gln Leu Gly Trp Asp His Trp Ile Ile Ala Pro Pro Phe Tyr
                        35                  40                  45

Thr Pro Asn Tyr Cys Lys Gly Thr Cys Leu Arg Val Leu Arg Asp Gly
                        50                  55                  60

Leu Asn Ser Pro Asn His Ala Ile Ile Gln Asn Leu Ile Asn Gln Leu
        65                      70                  75                  80

Val Asp Gln Ser Val Pro Arg Pro Ser Cys Val Pro Tyr Lys Tyr Val
                        85                  90                  95

Pro Ile Ser Val Leu Met Ile Glu Ala Asn Gly Ser Ile Leu Tyr Lys
                        100                 105                 110

Glu Tyr Glu Gly Met Ile Ala Gly Ser Cys Thr Cys Arg
                        115                 120                 125

<210> SEQ ID NO 22
<211> LENGTH: 119
<212> TYPE: PRT
<213> ORGANISM: Homo sapiens

<400> SEQUENCE: 22

Asp Ala Glu Pro Val Leu Gly Gly Pro Gly Gly Ala Cys Arg Ala
        1               5                   10                  15

Arg Arg Leu Tyr Val Ser Phe Arg Glu Val Gly Trp His Arg Trp Val
                        20                  25                  30

Ile Ala Pro Arg Gly Phe Leu Ala Asn Tyr Cys Gln Gly Gln Cys Ala
                        35                  40                  45

Leu Pro Val Ala Leu Ser Gly Ser Gly Gly Pro Pro Ala Leu Asn His
                        50                  55                  60

Ala Val Leu Arg Ala Leu Met His Ala Ala Ala Pro Gly Ala Ala Asp
        65                      70                  75                  80

Leu Pro Cys Cys Val Pro Ala Arg Leu Ser Pro Ile Ser Val Leu Phe
                        85                  90                  95

Phe Asp Asn Ser Asp Asn Val Val Leu Arg Gln Tyr Glu Asp Met Val
```

```
                        100                 105                 110

Val Asp Glu Cys Gly Cys Arg
            115

<210> SEQ ID NO 23
<211> LENGTH: 114
<212> TYPE: PRT
<213> ORGANISM: Homo sapiens

<400> SEQUENCE: 23

Ala Ala Ile Pro Val Pro Lys Leu Ser Cys Lys Asn Leu Cys His Arg
1               5                   10                  15

His Gln Leu Phe Ile Asn Phe Arg Asp Leu Gly Trp His Lys Trp Ile
            20                  25                  30

Ile Ala Pro Lys Gly Phe Met Ala Asn Tyr Cys His Gly Glu Cys Pro
        35                  40                  45

Phe Ser Leu Thr Ile Ser Leu Asn Ser Ser Asn Tyr Ala Phe Met Gln
    50                  55                  60

Ala Leu Met His Ala Val Asp Pro Glu Ile Pro Gln Ala Val Cys Ile
65                  70                  75                  80

Pro Thr Lys Leu Ser Pro Ile Ser Met Leu Tyr Gln Asp Asn Asn Asp
                85                  90                  95

Asn Val Ile Leu Arg His Tyr Glu Asp Met Val Val Asp Glu Cys Gly
            100                 105                 110

Cys Gly

<210> SEQ ID NO 24
<211> LENGTH: 120
<212> TYPE: PRT
<213> ORGANISM: Homo sapiens

<400> SEQUENCE: 24

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
    50                  55                  60

His Ala Val Ile Gln Thr Leu Met Asn Ser Met Asp Pro Glu Ser Thr
65                  70                  75                  80

Pro Pro Thr Ala Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
            115                 120

<210> SEQ ID NO 25
<211> LENGTH: 120
<212> TYPE: PRT
<213> ORGANISM: Homo sapiens

<400> SEQUENCE: 25

Thr Ala Phe Ala Ser Arg His Gly Lys Arg His Gly Lys Lys Ser Arg
1               5                   10                  15
```

```
Leu Arg Cys Ser Lys Lys Pro Leu His Val Asn Phe Lys Glu Leu Gly
            20                  25                  30

Trp Asp Asp Trp Ile Ile Ala Pro Leu Glu Tyr Glu Ala Tyr His Cys
            35                  40                  45

Glu Gly Val Cys Asp Phe Pro Leu Arg Ser His Leu Glu Pro Thr Asn
50                  55                  60

His Ala Ile Ile Gln Thr Leu Met Asn Ser Met Asp Pro Gly Ser Thr
65                  70                  75                  80

Pro Pro Ser Cys Cys Val Pro Thr Lys Leu Thr Pro Ile Ser Ile Leu
            85                  90                  95

Tyr Ile Asp Ala Gly Asn Asn Val Val Tyr Lys Gln Tyr Glu Asp Met
            100                 105                 110

Val Val Glu Ser Cys Gly Cys Arg
            115                 120

<210> SEQ ID NO 26
<211> LENGTH: 129
<212> TYPE: PRT
<213> ORGANISM: Homo sapiens

<400> SEQUENCE: 26

Thr Ala Leu Ala Gly Thr Arg Thr Ala Gln Gly Ser Gly Gly Gly Ala
1               5                   10                  15

Gly Arg Gly His Gly Arg Arg Gly Arg Ser Arg Cys Ser Arg Lys Pro
            20                  25                  30

Leu His Val Asp Phe Lys Glu Leu Gly Trp Asp Asp Trp Ile Ile Ala
            35                  40                  45

Pro Leu Asp Tyr Glu Ala Tyr His Cys Glu Gly Leu Cys Asp Phe Pro
50                  55                  60

Leu Arg Ser His Leu Glu Pro Thr Asn His Ala Ile Ile Gln Thr Leu
65                  70                  75                  80

Leu Asn Ser Met Ala Pro Asp Ala Ala Pro Ala Ser Cys Cys Val Pro
            85                  90                  95

Ala Arg Leu Ser Pro Ile Ser Ile Leu Tyr Ile Asp Ala Ala Asn Asn
            100                 105                 110

Val Val Tyr Lys Gln Tyr Glu Asp Met Val Val Glu Ala Cys Gly Cys
            115                 120                 125

Arg

<210> SEQ ID NO 27
<211> LENGTH: 109
<212> TYPE: PRT
<213> ORGANISM: Homo sapiens

<400> SEQUENCE: 27

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
```

-continued

```
                 85                  90                  95

Lys Ile Pro Ala Met Val Val Asp Arg Cys Gly Cys Ser
            100                 105

<210> SEQ ID NO 28
<211> LENGTH: 135
<212> TYPE: PRT
<213> ORGANISM: Homo sapiens

<400> SEQUENCE: 28

Gly Gln Glu Thr Val Ser Ser Glu Leu Lys Lys Pro Leu Gly Pro Ala
1               5                   10                  15

Ser Phe Asn Leu Ser Glu Tyr Phe Arg Gln Phe Leu Leu Pro Gln Asn
            20                  25                  30

Glu Cys Glu Leu His Asp Phe Arg Leu Ser Phe Ser Gln Leu Lys Trp
        35                  40                  45

Asp Asn Trp Ile Val Ala Pro His Arg Tyr Asn Pro Arg Tyr Cys Lys
    50                  55                  60

Gly Asp Cys Pro Arg Ala Val Gly His Arg Tyr Gly Ser Pro Val His
65                  70                  75                  80

Thr Met Val Gln Asn Ile Ile Tyr Glu Lys Leu Asp Ser Ser Val Pro
                85                  90                  95

Arg Pro Ser Cys Val Pro Ala Lys Tyr Ser Pro Leu Ser Val Leu Thr
            100                 105                 110

Ile Glu Pro Asp Gly Ser Ile Ala Tyr Lys Glu Tyr Glu Asp Met Ile
        115                 120                 125

Ala Thr Lys Cys Thr Cys Arg
    130                 135

<210> SEQ ID NO 29
<211> LENGTH: 119
<212> TYPE: PRT
<213> ORGANISM: Homo sapiens

<400> SEQUENCE: 29

Lys Thr Met Gln Lys Ala Arg Arg Lys Gln Trp Asp Glu Pro Arg Val
1               5                   10                  15

Cys Ser Arg Arg Tyr Leu Lys Val Asp Phe Ala Asp Ile Gly Trp Asn
            20                  25                  30

Glu Trp Ile Ile Ser Pro Lys Ser Phe Asp Ala Tyr Tyr Cys Ala Gly
        35                  40                  45

Ala Cys Glu Phe Pro Met Pro Lys Ile Val Arg Pro Ser Asn His Ala
    50                  55                  60

Thr Ile Gln Ser Ile Val Arg Ala Val Gly Ile Ile Pro Gly Ile Pro
65                  70                  75                  80

Glu Pro Cys Cys Val Pro Asp Lys Met Asn Ser Leu Gly Val Leu Phe
                85                  90                  95

Leu Asp Glu Asn Arg Asn Val Val Leu Lys Val Tyr Pro Asn Met Ser
            100                 105                 110

Val Asp Thr Cys Ala Cys Arg
        115

<210> SEQ ID NO 30
<211> LENGTH: 109
<212> TYPE: PRT
<213> ORGANISM: Homo sapiens

<400> SEQUENCE: 30
```

```
Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
            35                  40                  45

Tyr Met Phe Met Gln Lys Tyr Pro His Thr His Leu Val Gln Gln Ala
50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105
```

<210> SEQ ID NO 31
<211> LENGTH: 112
<212> TYPE: PRT
<213> ORGANISM: Homo sapiens

<400> SEQUENCE: 31

```
Ala Arg Asn Gly Asp Asp Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 32
<211> LENGTH: 110
<212> TYPE: PRT
<213> ORGANISM: Homo sapiens

<400> SEQUENCE: 32

```
His His Leu Pro Asp Arg Ser Gln Leu Cys Arg Lys Val Lys Phe Gln
1               5                   10                  15

Val Asp Phe Asn Leu Ile Gly Trp Gly Ser Trp Ile Ile Tyr Pro Lys
            20                  25                  30

Gln Tyr Asn Ala Tyr Arg Cys Glu Gly Glu Cys Pro Asn Pro Val Gly
            35                  40                  45

Glu Glu Phe His Pro Thr Asn His Ala Tyr Ile Gln Ser Leu Leu Lys
50                  55                  60

Arg Tyr Gln Pro His Arg Val Pro Ser Thr Cys Cys Ala Pro Val Lys
65                  70                  75                  80

Thr Lys Pro Leu Ser Met Leu Tyr Val Asp Asn Gly Arg Val Leu Leu
                85                  90                  95

Asp His His Lys Asp Met Ile Val Glu Glu Cys Gly Cys Leu
            100                 105                 110
```

```
<210> SEQ ID NO 33
<211> LENGTH: 116
<212> TYPE: PRT
<213> ORGANISM: Homo sapiens

<400> SEQUENCE: 33

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile Ala Pro
            20                  25                  30

Ser Gly Tyr His Ala Asn Tyr Cys Glu Gly Glu Cys Pro Ser His Ile
        35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
65                  70                  75                  80

Cys Val Pro Thr Lys Leu Arg Pro Met Ser Met Leu Tyr Tyr Asp Asp
                85                  90                  95

Gly Gln Asn Ile Ile Lys Lys Asp Ile Gln Asn Met Ile Val Glu Glu
            100                 105                 110

Cys Gly Cys Ser
            115

<210> SEQ ID NO 34
<211> LENGTH: 113
<212> TYPE: PRT
<213> ORGANISM: Homo sapiens

<400> SEQUENCE: 34

Arg Ala Leu Asp Thr Asn Tyr Cys Phe Ser Ser Thr Glu Lys Asn Cys
1               5                   10                  15

Cys Val Arg Gln Leu Tyr Ile Asp Phe Arg Lys Asp Leu Gly Trp Lys
            20                  25                  30

Trp Ile His Glu Pro Lys Gly Tyr His Ala Asn Phe Cys Leu Gly Pro
        35                  40                  45

Cys Pro Tyr Ile Trp Ser Leu Asp Thr Gln Tyr Ser Lys Val Leu Ala
    50                  55                  60

Leu Tyr Asn Gln His Asn Pro Gly Ala Ser Ala Ala Pro Cys Cys Val
65                  70                  75                  80

Pro Gln Ala Leu Glu Pro Leu Pro Ile Val Tyr Tyr Val Gly Arg Lys
                85                  90                  95

Pro Lys Val Glu Gln Leu Ser Asn Met Ile Val Arg Ser Cys Lys Cys
            100                 105                 110

Ser

<210> SEQ ID NO 35
<211> LENGTH: 112
<212> TYPE: PRT
<213> ORGANISM: Homo sapiens

<400> SEQUENCE: 35

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
```

```
                    35                  40                  45
Pro Tyr Leu Trp Ser Ser Asp Thr Gln His Ser Arg Val Leu Ser Leu
                50                  55                  60

Tyr Asn Thr Ile Asn Pro Glu Ala Ser Ala Ser Pro Cys Cys Val Ser
 65                  70                  75                  80

Gln Asp Leu Glu Pro Leu Thr Ile Leu Tyr Tyr Ile Gly Lys Thr Pro
                    85                  90                  95

Lys Ile Glu Gln Leu Ser Asn Met Ile Val Lys Ser Cys Lys Cys Ser
                100                 105                 110

<210> SEQ ID NO 36
<211> LENGTH: 112
<212> TYPE: PRT
<213> ORGANISM: Homo sapiens

<400> SEQUENCE: 36

Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Trp Lys Trp
                    20                  25                  30

Val His Glu Pro Lys Gly Tyr Tyr Ala Asn Phe Cys Ser Gly Pro Cys
                35                  40                  45

Pro Tyr Leu Arg Ser Ala Asp Thr Thr His Ser Thr Val Leu Gly Leu
                50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                    85                  90                  95

Lys Val Glu Gln Leu Ser Asn Met Val Val Lys Ser Cys Lys Cys Ser
                100                 105                 110
```